US009730791B2

(12) United States Patent
Ratz et al.

(10) Patent No.: US 9,730,791 B2
(45) Date of Patent: Aug. 15, 2017

(54) PROSTHESIS FOR ATRAUMATICALLY GRASPING INTRALUMENAL TISSUE AND METHODS OF DELIVERY

(71) Applicant: Edwards Lifesciences CardiAQ LLC, Irvine, CA (US)

(72) Inventors: J. Brent Ratz, Winchester, MA (US); Arshad Quadri, West Hartford, CT (US); Luca Pesce, Huntington Beach, CA (US)

(73) Assignee: Edwards Lifesciences CardiAQ LLC, Irvine, CA (US)

( * ) Notice: Subject to any disclaimer, the term of this patent is extended or adjusted under 35 U.S.C. 154(b) by 0 days.

(21) Appl. No.: 14/197,590

(22) Filed: Mar. 5, 2014

(65) Prior Publication Data

US 2014/0277390 A1    Sep. 18, 2014

Related U.S. Application Data

(60) Provisional application No. 61/789,783, filed on Mar. 15, 2013, provisional application No. 61/782,707, (Continued)

(51) Int. Cl.
*A61F 2/24* (2006.01)

(52) U.S. Cl.
CPC .... *A61F 2/2418* (2013.01); *A61F 2220/0008* (2013.01); *A61F 2250/006* (2013.01); (Continued)

(58) Field of Classification Search
CPC .................. A61F 2/24; A61F 2/2409
See application file for complete search history.

(56) References Cited

U.S. PATENT DOCUMENTS

| 865,203 A | 9/1907 | Mustonen et al. |
|---|---|---|
| 1,306,391 A | 6/1919 | Romanoff |

(Continued)

FOREIGN PATENT DOCUMENTS

| CA | 2304325 A1 | 10/2000 |
|---|---|---|
| CA | 2 827 556 A1 | 7/2012 |

(Continued)

OTHER PUBLICATIONS

US 8,062,357, 11/2011, Salahieh et al. (withdrawn)

(Continued)

*Primary Examiner* — Thomas J Sweet
*Assistant Examiner* — Wade P Schutte
(74) *Attorney, Agent, or Firm* — Knobbe Martens Olson & Bear LLP

(57) ABSTRACT

A prosthesis can comprise an expandable frame, a plurality of distal anchors and a plurality of proximal anchors. The anchors can extend outwardly from the frame. The frame can be configured to radially expand and contract for deployment within a body cavity. The frame and anchors can have one of many different shapes and configurations. For example, when the frame is in an expanded configuration, the proximal anchors can extend a significant distance away from the exterior of the frame, such as a length equal to or greater than about one half the diameter of the frame. As another example, the anchors can have looped ends.

26 Claims, 5 Drawing Sheets

Related U.S. Application Data filed on Mar. 14, 2013, provisional application No. 61/798,115, filed on Mar. 15, 2013.

(52) U.S. Cl.
CPC ............... *A61F 2250/0039* (2013.01); *A61F 2250/0069* (2013.01)

(56) References Cited

U.S. PATENT DOCUMENTS

| | | | |
|---|---|---|---|
| 3,312,237 A | 4/1967 | Mon et al. |
| 3,657,744 A | 4/1972 | Ersek |
| 3,671,979 A | 6/1972 | Moulopoulos |
| 3,739,402 A | 6/1973 | Cooley et al. |
| 4,056,854 A | 11/1977 | Boretos et al. |
| 4,079,468 A | 3/1978 | Liotta et al. |
| 4,204,283 A | 5/1980 | Bellhouse et al. |
| 4,222,126 A | 9/1980 | Boretos et al. |
| 4,265,694 A | 5/1981 | Boretos et al. |
| 4,339,831 A | 7/1982 | Johnson |
| 4,340,977 A | 7/1982 | Brownlee et al. |
| 4,470,157 A | 9/1984 | Love |
| 4,477,930 A | 10/1984 | Totten et al. |
| 4,490,859 A | 1/1985 | Black et al. |
| 4,553,545 A | 11/1985 | Maass et al. |
| 4,655,771 A | 4/1987 | Wallsten |
| 4,733,665 A | 3/1988 | Palmaz |
| 4,776,337 A | 10/1988 | Palmaz |
| 4,777,951 A | 10/1988 | Cribier et al. |
| 4,865,600 A | 9/1989 | Carpentier et al. |
| 4,908,028 A | 3/1990 | Colon et al. |
| 4,950,227 A | 8/1990 | Savin et al. |
| 4,994,077 A | 2/1991 | Dobben |
| 5,049,154 A | 9/1991 | Quadri |
| 5,133,725 A | 7/1992 | Quadri |
| 5,197,978 A | 3/1993 | Hess |
| 5,282,826 A | 2/1994 | Quadri |
| 5,326,371 A | 7/1994 | Love et al. |
| 5,332,402 A | 7/1994 | Teitelbaum |
| 5,344,427 A | 9/1994 | Cottenceau et al. |
| 5,370,685 A | 12/1994 | Stevens |
| 5,397,355 A | 3/1995 | Marin |
| 5,411,552 A | 5/1995 | Andersen et al. |
| 5,415,667 A | 5/1995 | Frater |
| 5,439,446 A | 8/1995 | Barry |
| 5,449,385 A | 9/1995 | Religa et al. |
| 5,474,563 A | 12/1995 | Myler et al. |
| 5,509,930 A | 4/1996 | Love |
| 5,545,214 A | 8/1996 | Stevens |
| 5,554,185 A | 9/1996 | Block et al. |
| 5,575,818 A | 11/1996 | Pinchuk |
| 5,607,444 A | 3/1997 | Lam |
| 5,607,469 A | 3/1997 | Frey |
| 5,669,919 A | 9/1997 | Sanders et al. |
| 5,697,382 A | 12/1997 | Love et al. |
| D390,957 S | 2/1998 | Fontaine |
| 5,713,952 A | 2/1998 | Vanney et al. |
| 5,725,519 A | 3/1998 | Penner |
| 5,769,812 A | 6/1998 | Stevens et al. |
| 5,807,398 A | 9/1998 | Shaknovich |
| 5,810,873 A | 9/1998 | Morales |
| 5,840,081 A | 11/1998 | Andersen et al. |
| 5,855,601 A | 1/1999 | Bessler et al. |
| 5,868,777 A | 2/1999 | Lam |
| 5,868,782 A | 2/1999 | Frantzen |
| 5,876,437 A | 3/1999 | Vanney et al. |
| 5,879,381 A | 3/1999 | Moriuch et al. |
| 5,902,334 A | 5/1999 | Dwyer et al. |
| 5,935,108 A | 8/1999 | Katoh |
| 5,954,764 A | 9/1999 | Parodi |
| 5,957,949 A | 9/1999 | Leonhardt et al. |
| 5,992,000 A | 11/1999 | Humphrey et al. |
| 6,004,328 A | 12/1999 | Solar |
| 6,015,431 A | 1/2000 | Thornton et al. |
| 6,042,606 A | 3/2000 | Frantzen |
| 6,053,940 A | 4/2000 | Wijay |
| 6,086,612 A | 7/2000 | Jansen |
| 6,113,612 A | 9/2000 | Swanson et al. |
| 6,113,631 A | 9/2000 | Jansen |
| 6,132,458 A | 10/2000 | Staehle et al. |
| 6,152,937 A | 11/2000 | Peterson et al. |
| 6,159,237 A | 12/2000 | Alt |
| 6,168,614 B1 | 1/2001 | Andersen et al. |
| 6,168,616 B1 | 1/2001 | Brown, III |
| 6,251,093 B1 | 6/2001 | Valley et al. |
| 6,280,466 B1 | 8/2001 | Kugler et al. |
| 6,306,141 B1 | 10/2001 | Jervis |
| 6,309,416 B1 | 10/2001 | Swanson et al. |
| 6,312,465 B1 | 11/2001 | Griffin et al. |
| 6,336,938 B1 | 1/2002 | Kavteladze et al. |
| 6,352,543 B1 | 3/2002 | Cole |
| 6,358,277 B1 | 3/2002 | Duran |
| 6,409,759 B1 | 6/2002 | Peredo |
| 6,425,916 B1 | 7/2002 | Garrison et al. |
| 6,440,163 B1 | 8/2002 | Swanson et al. |
| 6,440,164 B1 | 8/2002 | DeMatteo et al. |
| 6,454,799 B1 | 9/2002 | Schreck |
| 6,458,153 B1 | 10/2002 | Bailey et al. |
| 6,475,237 B2 | 11/2002 | Drasler et al. |
| 6,482,228 B1 | 11/2002 | Norred |
| 6,511,491 B2 | 1/2003 | Grudem et al. |
| 6,517,573 B1 | 2/2003 | Pollock |
| 6,527,800 B1 | 3/2003 | McGuckin, Jr. et al. |
| 6,533,812 B2 | 3/2003 | Swanson et al. |
| 6,551,303 B1 | 4/2003 | Van Tassei et al. |
| 6,582,462 B1 | 6/2003 | Andersen et al. |
| 6,602,281 B1 | 8/2003 | Klein |
| 6,610,088 B1 | 8/2003 | Gabbay |
| 6,641,606 B2 | 11/2003 | Ouriel et al. |
| 6,652,578 B2 | 11/2003 | Bailey et al. |
| D484,979 S | 1/2004 | Fontaine |
| 6,676,698 B2 | 1/2004 | McGuckin et al. |
| 6,682,537 B2 | 1/2004 | Ouriel et al. |
| 6,695,878 B2 | 2/2004 | McGuckin et al. |
| 6,712,836 B1 | 3/2004 | Berg et al. |
| 6,723,123 B1 | 4/2004 | Kazatchkov et al. |
| 6,730,118 B2 | 5/2004 | Spenser et al. |
| 6,733,523 B2 | 5/2004 | Shaolian et al. |
| 6,764,505 B1 | 7/2004 | Hossainy et al. |
| 6,767,362 B2 | 7/2004 | Schreck |
| 6,780,200 B2 | 8/2004 | Jansen |
| 6,790,229 B1 | 9/2004 | Berreklouw |
| 6,790,230 B2 | 9/2004 | Beyersdorf et al. |
| 6,814,746 B2 | 11/2004 | Thompson et al. |
| 6,830,584 B1 | 12/2004 | Sequin |
| 6,858,034 B1 | 2/2005 | Hijlkema et al. |
| 6,875,231 B2 | 4/2005 | Anduiza et al. |
| 6,893,460 B2 | 5/2005 | Spenser et al. |
| 6,908,477 B2 | 6/2005 | McGuckin, Jr. et al. |
| 6,908,481 B2 | 6/2005 | Cribier |
| 6,926,732 B2 | 8/2005 | Derus et al. |
| 6,929,660 B1 | 8/2005 | Ainsworth et al. |
| 6,936,058 B2 | 8/2005 | Forde et al. |
| 6,960,219 B2 | 11/2005 | Grudem et al. |
| 6,979,350 B2 | 12/2005 | Moll et al. |
| 7,014,653 B2 | 3/2006 | Ouriel et al. |
| 7,018,401 B1 | 3/2006 | Hyodoh et al. |
| 7,018,406 B2 | 3/2006 | Seguin et al. |
| 7,025,780 B2 | 4/2006 | Gabbay |
| 7,044,134 B2 | 5/2006 | Khairkhahan et al. |
| 7,044,962 B2 | 5/2006 | Elliott |
| 7,044,966 B2 | 5/2006 | Svanidze et al. |
| 7,087,088 B2 | 8/2006 | Berg et al. |
| 7,147,660 B2 | 12/2006 | Chobotov et al. |
| 7,147,661 B2 | 12/2006 | Chobotov et al. |
| 7,153,322 B2 | 12/2006 | Alt |
| 7,186,265 B2 | 3/2007 | Sharkawy et al. |
| 7,198,646 B2 | 4/2007 | Figulla et al. |
| 7,201,772 B2 | 4/2007 | Schwammenthal et al. |
| 7,232,449 B2 | 6/2007 | Sharkawy et al. |
| 7,252,682 B2 | 8/2007 | Seguin |
| D553,747 S | 10/2007 | Fliedner |
| 7,276,078 B2 | 10/2007 | Spenser et al. |
| 7,276,084 B2 | 10/2007 | Yang et al. |

(56) References Cited

U.S. PATENT DOCUMENTS

| | | |
|---|---|---|
| 7,328,270 B1 | 2/2008 | Reents et al. |
| 7,329,278 B2 | 2/2008 | Seguin et al. |
| 7,374,571 B2 | 5/2008 | Pease et al. |
| 7,381,219 B2 | 6/2008 | Salahieh et al. |
| 7,393,360 B2 | 7/2008 | Spenser et al. |
| 7,422,602 B2 | 9/2008 | Grudem et al. |
| 7,425,219 B2 | 9/2008 | Quadri |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,510,575 B2 | 3/2009 | Spenser et al. |
| 7,524,330 B2 | 4/2009 | Berreklouw |
| 7,534,261 B2 | 5/2009 | Friedman |
| 7,585,321 B2 | 9/2009 | Cribier |
| 7,608,114 B2 | 10/2009 | Levine et al. |
| 7,615,072 B2 | 11/2009 | Rust et al. |
| 7,618,446 B2 | 11/2009 | Andersen et al. |
| 7,628,805 B2 | 12/2009 | Spenser et al. |
| 7,632,298 B2 | 12/2009 | Hijlkema et al. |
| 7,748,389 B2 | 7/2010 | Salahieh et al. |
| 7,753,949 B2 | 7/2010 | Lamphere et al. |
| D622,387 S | 8/2010 | Igaki |
| D622,388 S | 8/2010 | Igaki |
| 7,771,463 B2 | 8/2010 | Ton et al. |
| 7,771,472 B2 | 8/2010 | Hedricksen et al. |
| 7,785,360 B2 | 8/2010 | Freitag |
| 7,803,185 B2 | 9/2010 | Gabbay |
| 7,806,917 B2 | 10/2010 | Xiao |
| 7,806,919 B2 | 10/2010 | Bloom et al. |
| 7,815,589 B2 | 10/2010 | Meade et al. |
| 7,815,673 B2 | 10/2010 | Bloom et al. |
| 7,824,443 B2 | 11/2010 | Salahieh et al. |
| 7,846,203 B2 | 12/2010 | Cribier |
| 7,871,435 B2 | 1/2011 | Carpentier |
| 7,892,281 B2 | 2/2011 | Seguin et al. |
| D635,261 S | 3/2011 | Rossi |
| D635,262 S | 3/2011 | Rossi |
| 7,914,569 B2 | 3/2011 | Nguyen et al. |
| 7,947,075 B2 | 5/2011 | Goetz et al. |
| 7,959,672 B2 | 6/2011 | Salahieh et al. |
| 7,972,377 B2 | 7/2011 | Lane |
| 7,972,378 B2 | 7/2011 | Tabor et al. |
| 7,981,151 B2 | 7/2011 | Rowe |
| 7,993,392 B2 | 8/2011 | Righini et al. |
| 7,993,394 B2 | 8/2011 | Hariton et al. |
| 8,016,870 B2 | 9/2011 | Chew et al. |
| 8,016,877 B2 | 9/2011 | Seguin et al. |
| 8,048,153 B2 | 11/2011 | Salahieh et al. |
| 8,052,750 B2 | 11/2011 | Tuval et al. |
| 8,070,800 B2 | 12/2011 | Lock et al. |
| 8,070,802 B2 | 12/2011 | Lamphere et al. |
| 8,075,615 B2 | 12/2011 | Eberhardt et al. |
| 8,080,054 B2 | 12/2011 | Rowe |
| 8,092,520 B2 | 1/2012 | Quadri |
| 8,109,996 B2 | 2/2012 | Stacchino |
| 8,136,218 B2 | 3/2012 | Millwee et al. |
| 8,137,398 B2 | 3/2012 | Tuval et al. |
| 8,157,852 B2 | 4/2012 | Bloom et al. |
| 8,167,926 B2 | 5/2012 | Hartley et al. |
| 8,167,932 B2 | 5/2012 | Bourang et al. |
| 8,167,934 B2 | 5/2012 | Styrc et al. |
| 8,177,799 B2 | 5/2012 | Orban, III |
| 8,182,528 B2 | 5/2012 | Salahieh et al. |
| 8,182,530 B2 | 5/2012 | Huber |
| 8,216,261 B2 | 7/2012 | Solem |
| 8,216,301 B2 | 7/2012 | Bonhoeffer et al. |
| 8,219,229 B2 | 7/2012 | Cao et al. |
| 8,220,121 B2 | 7/2012 | Hendriksen et al. |
| 8,221,482 B2 | 7/2012 | Cottone et al. |
| 8,221,493 B2 | 7/2012 | Boyle et al. |
| 8,226,710 B2 | 7/2012 | Nguyen et al. |
| D665,079 S | 8/2012 | Zago |
| D665,080 S | 8/2012 | Zago |
| 8,236,045 B2 | 8/2012 | Benichou et al. |
| 8,246,675 B2 | 8/2012 | Zegdi |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,287,584 B2 | 10/2012 | Salahieh et al. |
| 8,303,653 B2 | 11/2012 | Bonhoeffer et al. |
| 8,313,525 B2 | 11/2012 | Tuval et al. |
| 8,317,854 B1 | 11/2012 | Ryan et al. |
| 8,323,335 B2 | 12/2012 | Rowe et al. |
| 8,337,541 B2 | 12/2012 | Quadri et al. |
| 8,353,953 B2 | 1/2013 | Giannetti et al. |
| 8,361,137 B2 | 1/2013 | Perouse |
| 8,361,537 B2 | 1/2013 | Shanley |
| 8,398,708 B2 | 3/2013 | Meiri et al. |
| 8,403,983 B2 | 3/2013 | Quadri et al. |
| 8,408,214 B2 | 4/2013 | Spenser |
| 8,414,644 B2 | 4/2013 | Quadri et al. |
| 8,414,645 B2 | 4/2013 | Dwork et al. |
| 8,444,689 B2 | 5/2013 | Zhang |
| 8,449,466 B2 | 5/2013 | Duhay et al. |
| 8,449,599 B2 | 5/2013 | Chau et al. |
| 8,449,625 B2 | 5/2013 | Campbell et al. |
| 8,454,685 B2 | 6/2013 | Hariton et al. |
| 8,470,023 B2 | 6/2013 | Eidenschink et al. |
| 8,470,024 B2 | 6/2013 | Ghione et al. |
| 8,475,521 B2 | 7/2013 | Suri et al. |
| 8,475,523 B2 | 7/2013 | Duffy |
| 8,479,380 B2 | 7/2013 | Malewicz et al. |
| 8,491,650 B2 | 7/2013 | Wiemeyer et al. |
| 8,500,798 B2 | 8/2013 | Rowe et al. |
| 8,511,244 B2 | 8/2013 | Holecek et al. |
| 8,512,401 B2 | 8/2013 | Murray, III et al. |
| 8,518,106 B2 | 8/2013 | Duffy et al. |
| 8,535,368 B2 | 9/2013 | Headley, Jr. et al. |
| 8,562,663 B2 | 10/2013 | Mearns et al. |
| 8,579,964 B2 | 11/2013 | Lane et al. |
| 8,579,965 B2 | 11/2013 | Bonhoeffer et al. |
| 8,584,849 B2 | 11/2013 | McCaffrey |
| 8,585,749 B2 | 11/2013 | Shelso |
| 8,585,755 B2 | 11/2013 | Chau et al. |
| 8,585,756 B2 | 11/2013 | Bonhoeffer et al. |
| 8,591,570 B2 | 11/2013 | Revuelta et al. |
| 8,597,348 B2 | 12/2013 | Rowe et al. |
| 8,617,236 B2 | 12/2013 | Paul et al. |
| 8,623,075 B2 | 1/2014 | Murray, III et al. |
| 8,640,521 B2 | 2/2014 | Righini et al. |
| 8,647,381 B2 | 2/2014 | Essinger et al. |
| 8,652,145 B2 | 2/2014 | Maimon et al. |
| 8,652,201 B2 | 2/2014 | Oberti et al. |
| 8,652,202 B2 | 2/2014 | Alon et al. |
| 8,652,203 B2 | 2/2014 | Quadri et al. |
| 8,668,730 B2 | 3/2014 | McGuckin, Jr. et al. |
| 8,668,733 B2 | 3/2014 | Haug et al. |
| 8,672,992 B2 | 3/2014 | Orr |
| 8,673,000 B2 | 3/2014 | Tabor et al. |
| 8,679,174 B2 | 3/2014 | Ottma et al. |
| 8,679,404 B2 | 3/2014 | Liburd et al. |
| 8,685,086 B2 | 4/2014 | Navia et al. |
| 8,707,957 B2 | 4/2014 | Callister et al. |
| 8,721,707 B2 | 5/2014 | Boucher et al. |
| 8,721,708 B2 | 5/2014 | Sequin et al. |
| 8,721,714 B2 | 5/2014 | Kelley |
| 8,728,154 B2 | 5/2014 | Alkhatib |
| 8,728,155 B2 | 5/2014 | Montorfano et al. |
| 8,740,974 B2 | 6/2014 | Lambrecht et al. |
| 8,740,976 B2 | 6/2014 | Tran et al. |
| 8,747,458 B2 | 6/2014 | Tuval et al. |
| 8,747,459 B2 | 6/2014 | Nguyen et al. |
| 8,747,460 B2 | 6/2014 | Tuval et al. |
| 8,753,384 B2 | 6/2014 | Leanna |
| 8,758,432 B2 | 6/2014 | Solem |
| 8,764,814 B2 | 7/2014 | Solem |
| 8,764,818 B2 | 7/2014 | Gregg |
| 8,771,344 B2 | 7/2014 | Tran et al. |
| 8,771,345 B2 | 7/2014 | Tuval et al. |
| 8,771,346 B2 | 7/2014 | Tuval et al. |
| 8,777,975 B2 | 7/2014 | Kashkarov et al. |
| 8,778,020 B2 | 7/2014 | Gregg et al. |
| 8,784,478 B2 | 7/2014 | Tuval et al. |

(56) References Cited

U.S. PATENT DOCUMENTS

| | | |
|---|---|---|
| 8,784,481 B2 | 7/2014 | Alkhatib et al. |
| 8,790,387 B2 | 7/2014 | Nguyen et al. |
| 8,795,356 B2 | 8/2014 | Quadri et al. |
| 8,795,357 B2 | 8/2014 | Yohanan et al. |
| 8,828,078 B2 | 9/2014 | Salahieh et al. |
| 8,828,079 B2 | 9/2014 | Thielen et al. |
| 8,834,564 B2 | 9/2014 | Tuval et al. |
| 8,845,718 B2 | 9/2014 | Tuval et al. |
| 8,852,267 B2 | 10/2014 | Cattaneo |
| 8,870,947 B2 | 10/2014 | Shaw |
| 8,870,948 B1 | 10/2014 | Erzberger et al. |
| 8,876,883 B2 | 11/2014 | Rust |
| 8,876,893 B2 | 11/2014 | Dwork et al. |
| 8,876,895 B2 | 11/2014 | Tuval et al. |
| 8,894,702 B2 | 11/2014 | Quadri et al. |
| 8,911,455 B2 | 12/2014 | Quadri et al. |
| 8,926,693 B2 | 1/2015 | Duffy et al. |
| 8,926,694 B2 | 1/2015 | Costello |
| 8,945,209 B2 | 2/2015 | Bonyuet et al. |
| 8,951,299 B2 | 2/2015 | Paul et al. |
| 8,961,583 B2 | 2/2015 | Hojeibane et al. |
| 8,961,593 B2 | 2/2015 | Bonhoeffer et al. |
| 8,961,595 B2 | 2/2015 | Alkhatib |
| 8,974,524 B2 | 3/2015 | Yeung et al. |
| 8,979,922 B2 | 3/2015 | Jayasinghe et al. |
| 8,986,375 B2 | 3/2015 | Garde et al. |
| 8,992,608 B2 | 3/2015 | Haug et al. |
| 8,998,979 B2 | 4/2015 | Seguin et al. |
| 8,998,980 B2 | 4/2015 | Shipley et al. |
| 9,005,270 B2 | 4/2015 | Perkins et al. |
| 9,005,273 B2 | 4/2015 | Salahieh et al. |
| 9,011,521 B2 | 4/2015 | Haug et al. |
| 9,011,523 B2 | 4/2015 | Seguin |
| 9,011,524 B2 | 4/2015 | Eberhardt |
| 9,023,100 B2 | 5/2015 | Quadri et al. |
| 9,028,545 B2 | 5/2015 | Taylor |
| 9,029,418 B2 | 5/2015 | Dove et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,055,937 B2 | 6/2015 | Rowe et al. |
| 9,078,749 B2 | 7/2015 | Lutter et al. |
| 9,078,751 B2 | 7/2015 | Naor |
| 9,125,738 B2 | 9/2015 | Figulla et al. |
| 9,138,312 B2 | 9/2015 | Tuval et al. |
| 9,161,834 B2 | 10/2015 | Taylor et al. |
| 2001/0007956 A1 | 7/2001 | Letac et al. |
| 2001/0021872 A1 | 9/2001 | Bailey et al. |
| 2001/0047180 A1 | 11/2001 | Grudem et al. |
| 2001/0047200 A1 | 11/2001 | White |
| 2002/0016623 A1 | 2/2002 | Kula et al. |
| 2002/0022853 A1 | 2/2002 | Swanson et al. |
| 2002/0032481 A1 | 3/2002 | Gabbay |
| 2002/0045929 A1 | 4/2002 | Diaz |
| 2002/0052644 A1 | 5/2002 | Shaolian et al. |
| 2002/0055772 A1 | 5/2002 | McGuckin et al. |
| 2002/0077695 A1 | 6/2002 | Swanson et al. |
| 2002/0111619 A1 | 8/2002 | Keast et al. |
| 2002/0111647 A1 | 8/2002 | Khairkhahan et al. |
| 2002/0183827 A1 | 12/2002 | Derus et al. |
| 2003/0014104 A1 | 1/2003 | Cribier |
| 2003/0040792 A1 | 2/2003 | Gabbay |
| 2003/0083679 A1 | 5/2003 | Grudem et al. |
| 2003/0105517 A1 | 6/2003 | White et al. |
| 2003/0109924 A1 | 6/2003 | Cribier |
| 2003/0114913 A1 | 6/2003 | Spenser et al. |
| 2003/0120263 A1 | 6/2003 | Ouriel et al. |
| 2003/0120330 A1 | 6/2003 | Ouriel et al. |
| 2003/0120333 A1 | 6/2003 | Ouriel et al. |
| 2003/0130729 A1 | 7/2003 | Paniagua |
| 2003/0176914 A1 | 9/2003 | Rabkin et al. |
| 2003/0187499 A1 | 10/2003 | Swanson et al. |
| 2003/0199971 A1 | 10/2003 | Tower et al. |
| 2003/0220683 A1 | 11/2003 | Minasian et al. |
| 2004/0039436 A1 | 2/2004 | Spenser et al. |
| 2004/0087900 A1 | 5/2004 | Thompson et al. |
| 2004/0093058 A1 | 5/2004 | Cottone et al. |
| 2004/0093060 A1 | 5/2004 | Seguin et al. |
| 2004/0102842 A1 | 5/2004 | Jansen |
| 2004/0117009 A1 | 6/2004 | Cali et al. |
| 2004/0133273 A1 | 7/2004 | Cox |
| 2004/0186561 A1 | 9/2004 | McGuckin, Jr. et al. |
| 2004/0193261 A1 | 9/2004 | Berreklou |
| 2004/0210304 A1 | 10/2004 | Seguin et al. |
| 2004/0210307 A1 | 10/2004 | Khairkhahan |
| 2004/0215325 A1 | 10/2004 | Penn et al. |
| 2004/0225353 A1 | 11/2004 | McGuckin, Jr. et al. |
| 2004/0236411 A1 | 11/2004 | Sarac et al. |
| 2004/0243230 A1 | 12/2004 | Navia et al. |
| 2004/0249433 A1 | 12/2004 | Freitag |
| 2005/0033398 A1 | 2/2005 | Seguin |
| 2005/0038470 A1 | 2/2005 | van der Burg et al. |
| 2005/0075727 A1 | 4/2005 | Wheatley |
| 2005/0090887 A1 | 4/2005 | Pryor |
| 2005/0096738 A1 | 5/2005 | Cali et al. |
| 2005/0107872 A1 | 5/2005 | Mensah et al. |
| 2005/0125020 A1 | 6/2005 | Meade et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137690 A1 | 6/2005 | Salahieh et al. |
| 2005/0137691 A1 | 6/2005 | Salahieh et al. |
| 2005/0137693 A1 | 6/2005 | Haug et al. |
| 2005/0137695 A1 | 6/2005 | Salahieh et al. |
| 2005/0137701 A1 | 6/2005 | Salahieh et al. |
| 2005/0154444 A1 | 7/2005 | Quadri |
| 2005/0159811 A1 | 7/2005 | Lane |
| 2005/0182483 A1 | 8/2005 | Osborne et al. |
| 2005/0182486 A1 | 8/2005 | Gabbay |
| 2005/0203616 A1 | 9/2005 | Cribier |
| 2005/0203618 A1 | 9/2005 | Sharkawy et al. |
| 2005/0216079 A1 | 9/2005 | Macoviak |
| 2005/0234546 A1 | 10/2005 | Nugent et al. |
| 2005/0240204 A1 | 10/2005 | Grudem et al. |
| 2005/0251251 A1 | 11/2005 | Cribier |
| 2005/0283231 A1 | 12/2005 | Haug et al. |
| 2006/0020247 A1 | 1/2006 | Kagan et al. |
| 2006/0020327 A1 | 1/2006 | Lashinski et al. |
| 2006/0020334 A1 | 1/2006 | Lashinski et al. |
| 2006/0052802 A1 | 3/2006 | Sterman et al. |
| 2006/0052867 A1 | 3/2006 | Revuelta et al. |
| 2006/0058872 A1 | 3/2006 | Salahieh et al. |
| 2006/0095115 A1 | 5/2006 | Bladillah et al. |
| 2006/0106454 A1 | 5/2006 | Osborne et al. |
| 2006/0116625 A1 | 6/2006 | Renati et al. |
| 2006/0129235 A1 | 6/2006 | Seguin et al. |
| 2006/0149360 A1 | 7/2006 | Schwammenthal et al. |
| 2006/0161265 A1 | 7/2006 | Levine et al. |
| 2006/0173537 A1 | 8/2006 | Yang et al. |
| 2006/0195183 A1 | 8/2006 | Navia et al. |
| 2006/0212110 A1 | 9/2006 | Osborne et al. |
| 2006/0224232 A1 | 10/2006 | Chobotov |
| 2006/0241745 A1 | 10/2006 | Solem |
| 2006/0253191 A1 | 11/2006 | Salahieh et al. |
| 2006/0259135 A1 | 11/2006 | Navia et al. |
| 2006/0259136 A1 | 11/2006 | Nguyen et al. |
| 2006/0265056 A1 | 11/2006 | Nguyen et al. |
| 2006/0287717 A1 | 12/2006 | Rowe et al. |
| 2006/0287719 A1 | 12/2006 | Rowe et al. |
| 2006/0293745 A1 | 12/2006 | Carpentier et al. |
| 2007/0010876 A1 | 1/2007 | Salahieh et al. |
| 2007/0016286 A1 | 1/2007 | Hermann et al. |
| 2007/0043435 A1 | 2/2007 | Seguin et al. |
| 2007/0050021 A1 | 3/2007 | Johnson |
| 2007/0067016 A1 | 3/2007 | Jung |
| 2007/0100432 A1 | 5/2007 | Case et al. |
| 2007/0118206 A1 | 5/2007 | Colgan et al. |
| 2007/0118207 A1 | 5/2007 | Amplatz et al. |
| 2007/0123798 A1 | 5/2007 | Rahamimov |
| 2007/0129794 A1 | 6/2007 | Realyvasquez |
| 2007/0142906 A1 | 6/2007 | Figulla et al. |
| 2007/0162107 A1 | 7/2007 | Haug et al. |
| 2007/0185559 A1 | 8/2007 | Shelso |
| 2007/0213813 A1 | 9/2007 | Von Segesser et al. |

(56) References Cited

U.S. PATENT DOCUMENTS

| | | |
|---|---|---|
| 2007/0219620 A1 | 9/2007 | Eells et al. |
| 2007/0233228 A1 | 10/2007 | Eberhardt et al. |
| 2007/0250151 A1 | 10/2007 | Pereira |
| 2007/0255391 A1 | 11/2007 | Hojeibane et al. |
| 2007/0255394 A1 | 11/2007 | Ryan |
| 2007/0270932 A1 | 11/2007 | Headley et al. |
| 2007/0270937 A1 | 11/2007 | Leanna |
| 2007/0293940 A1 | 12/2007 | Schaeffer et al. |
| 2008/0009934 A1 | 1/2008 | Schneider et al. |
| 2008/0021546 A1 | 1/2008 | Patz et al. |
| 2008/0071361 A1 | 3/2008 | Tuval et al. |
| 2008/0071363 A1 | 3/2008 | Tuval et al. |
| 2008/0071366 A1 | 3/2008 | Tuval et al. |
| 2008/0071369 A1 | 3/2008 | Tuval et al. |
| 2008/0082164 A1 | 4/2008 | Friedman |
| 2008/0082165 A1 | 4/2008 | Wilson et al. |
| 2008/0082166 A1 | 4/2008 | Styrc et al. |
| 2008/0097571 A1 | 4/2008 | Denison et al. |
| 2008/0097581 A1 | 4/2008 | Shanley |
| 2008/0114441 A1 | 5/2008 | Rust et al. |
| 2008/0125853 A1 | 5/2008 | Boyle et al. |
| 2008/0125859 A1 | 5/2008 | Salahieh et al. |
| 2008/0133003 A1 | 6/2008 | Seguin |
| 2008/0140189 A1 | 6/2008 | Nguyen et al. |
| 2008/0147179 A1 | 6/2008 | Cai et al. |
| 2008/0147183 A1 | 6/2008 | Styrc |
| 2008/0161911 A1 | 7/2008 | Revuelta et al. |
| 2008/0177381 A1 | 7/2008 | Navia et al. |
| 2008/0183273 A1 | 7/2008 | Mesana et al. |
| 2008/0208307 A1 | 8/2008 | Ben-Muvhar et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0228254 A1 | 9/2008 | Ryan |
| 2008/0243233 A1 | 10/2008 | Ben-Muvhar et al. |
| 2008/0243245 A1 | 10/2008 | Thambar et al. |
| 2008/0262596 A1 | 10/2008 | Xiao |
| 2008/0269878 A1 | 10/2008 | Iobbi |
| 2008/0275549 A1 | 11/2008 | Rowe |
| 2008/0275550 A1 | 11/2008 | Kheradvar et al. |
| 2009/0005863 A1 | 1/2009 | Goetz et al. |
| 2009/0012602 A1 | 1/2009 | Quadri |
| 2009/0054976 A1 | 2/2009 | Tuval et al. |
| 2009/0062908 A1 | 3/2009 | Bonhoeffer et al. |
| 2009/0076585 A1 | 3/2009 | Hendriksen |
| 2009/0076598 A1 | 3/2009 | Salahieh et al. |
| 2009/0082844 A1 | 3/2009 | Zacharias et al. |
| 2009/0082847 A1 | 3/2009 | Zacharias et al. |
| 2009/0088832 A1 | 4/2009 | Chew et al. |
| 2009/0088836 A1 | 4/2009 | Bishop et al. |
| 2009/0099643 A1 | 4/2009 | Hyodoh et al. |
| 2009/0099653 A1 | 4/2009 | Suri et al. |
| 2009/0125096 A1 | 5/2009 | Chu et al. |
| 2009/0125104 A1 | 5/2009 | Hoffman |
| 2009/0132035 A1 | 5/2009 | Roth et al. |
| 2009/0132037 A1 | 5/2009 | Hoffman et al. |
| 2009/0138069 A1 | 5/2009 | Hoffman |
| 2009/0138079 A1 | 5/2009 | Tuval et al. |
| 2009/0149946 A1 | 6/2009 | Dixon |
| 2009/0157175 A1 | 6/2009 | Benichou |
| 2009/0163934 A1 | 6/2009 | Raschdorf et al. |
| 2009/0171438 A1 | 7/2009 | Chuter et al. |
| 2009/0171456 A1 | 7/2009 | Kveen et al. |
| 2009/0177262 A1 | 7/2009 | Oberti et al. |
| 2009/0182407 A1 | 7/2009 | Leanna et al. |
| 2009/0182413 A1* | 7/2009 | Burkart et al. .............. 623/1.16 |
| 2009/0188964 A1 | 7/2009 | Orlov |
| 2009/0192601 A1 | 7/2009 | Rafiee et al. |
| 2009/0216314 A1 | 8/2009 | Quadri |
| 2009/0234443 A1 | 9/2009 | Ottma et al. |
| 2009/0248132 A1 | 10/2009 | Bloom et al. |
| 2009/0248133 A1 | 10/2009 | Bloom et al. |
| 2009/0264997 A1 | 10/2009 | Salahieh et al. |
| 2009/0270972 A1 | 10/2009 | Lane |
| 2009/0276040 A1 | 11/2009 | Rowe et al. |
| 2009/0281618 A1 | 11/2009 | Hill et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0292350 A1 | 11/2009 | Eberhardt et al. |
| 2009/0306768 A1 | 12/2009 | Quadri |
| 2010/0004740 A1 | 1/2010 | Sequin et al. |
| 2010/0036479 A1 | 2/2010 | Hill et al. |
| 2010/0049306 A1 | 2/2010 | House et al. |
| 2010/0082089 A1 | 4/2010 | Quadri et al. |
| 2010/0082094 A1 | 4/2010 | Quadri et al. |
| 2010/0094411 A1 | 4/2010 | Tuval et al. |
| 2010/0114299 A1 | 5/2010 | Ben Muvhar et al. |
| 2010/0114305 A1 | 5/2010 | Kang et al. |
| 2010/0121461 A1 | 5/2010 | Sobrino-Serrano et al. |
| 2010/0161027 A1 | 6/2010 | Orr |
| 2010/0179633 A1 | 7/2010 | Solem |
| 2010/0179647 A1 | 7/2010 | Carpenter et al. |
| 2010/0191326 A1 | 7/2010 | Alkhatib |
| 2010/0217382 A1 | 8/2010 | Chau et al. |
| 2010/0249894 A1 | 9/2010 | Oba et al. |
| 2010/0249911 A1 | 9/2010 | Alkhatib |
| 2010/0256723 A1 | 10/2010 | Murray |
| 2010/0262157 A1 | 10/2010 | Silver et al. |
| 2010/0274345 A1 | 10/2010 | Rust |
| 2010/0280606 A1 | 11/2010 | Naor |
| 2010/0298931 A1 | 11/2010 | Quadri et al. |
| 2010/0305685 A1 | 12/2010 | Millwee et al. |
| 2010/0312333 A1 | 12/2010 | Navia et al. |
| 2011/0004296 A1 | 1/2011 | Lutter et al. |
| 2011/0022157 A1 | 1/2011 | Essinger et al. |
| 2011/0022164 A1 | 1/2011 | Quinn et al. |
| 2011/0022165 A1 | 1/2011 | Oba et al. |
| 2011/0022166 A1 | 1/2011 | Dahlgren et al. |
| 2011/0022169 A1 | 1/2011 | Ryan et al. |
| 2011/0029067 A1 | 2/2011 | McGuckin, Jr. et al. |
| 2011/0137397 A1 | 6/2011 | Chau et al. |
| 2011/0166644 A1 | 7/2011 | Keeble et al. |
| 2011/0178597 A9 | 7/2011 | Navia et al. |
| 2011/0208297 A1 | 8/2011 | Tuval et al. |
| 2011/0208298 A1 | 8/2011 | Tuval et al. |
| 2011/0218619 A1 | 9/2011 | Benichou et al. |
| 2011/0224780 A1 | 9/2011 | Tabor et al. |
| 2011/0224785 A1 | 9/2011 | Hacohen |
| 2011/0264196 A1 | 10/2011 | Savage et al. |
| 2011/0313515 A1 | 12/2011 | Quadri et al. |
| 2011/0319989 A1 | 12/2011 | Lane et al. |
| 2012/0016411 A1 | 1/2012 | Tuval |
| 2012/0022639 A1 | 1/2012 | Hacohen et al. |
| 2012/0022640 A1 | 1/2012 | Gross et al. |
| 2012/0041550 A1 | 2/2012 | Salahieh et al. |
| 2012/0059452 A1 | 3/2012 | Boucher et al. |
| 2012/0059454 A1 | 3/2012 | Millwee et al. |
| 2012/0078353 A1 | 3/2012 | Quadri et al. |
| 2012/0078360 A1* | 3/2012 | Rafiee .......................... 623/2.37 |
| 2012/0101571 A1 | 4/2012 | Thambar et al. |
| 2012/0101572 A1 | 4/2012 | Kovalsky et al. |
| 2012/0123529 A1 | 5/2012 | Levi et al. |
| 2012/0179239 A1 | 7/2012 | Quadri et al. |
| 2012/0215303 A1 | 8/2012 | Quadri et al. |
| 2012/0259405 A1 | 10/2012 | Weber et al. |
| 2012/0271398 A1 | 10/2012 | Essinger et al. |
| 2012/0283824 A1 | 11/2012 | Lutter et al. |
| 2012/0290062 A1 | 11/2012 | McNamara et al. |
| 2012/0296418 A1 | 11/2012 | Bonyuet et al. |
| 2012/0303116 A1* | 11/2012 | Gorman, III .......... A61F 2/2418 623/2.11 |
| 2012/0310328 A1 | 12/2012 | Olson et al. |
| 2012/0323316 A1 | 12/2012 | Chau et al. |
| 2013/0006294 A1 | 1/2013 | Kashkarov |
| 2013/0018458 A1 | 1/2013 | Yohanan et al. |
| 2013/0053950 A1 | 2/2013 | Rowe et al. |
| 2013/0110227 A1 | 5/2013 | Quadri et al. |
| 2013/0131788 A1 | 5/2013 | Quadri et al. |
| 2013/0131793 A1 | 5/2013 | Quadri et al. |
| 2013/0138203 A1 | 5/2013 | Quadri et al. |
| 2013/0138207 A1 | 5/2013 | Quadri et al. |
| 2013/0144375 A1 | 6/2013 | Giasolli et al. |
| 2013/0144378 A1 | 6/2013 | Quadri et al. |

(56) References Cited

U.S. PATENT DOCUMENTS

| | | |
|---|---|---|
| 2013/0144380 A1 | 6/2013 | Quadri et al. |
| 2013/0144381 A1 | 6/2013 | Quadri et al. |
| 2013/0150956 A1 | 6/2013 | Yohanan et al. |
| 2013/0172983 A1 | 7/2013 | Clerc et al. |
| 2013/0184811 A1 | 7/2013 | Rowe et al. |
| 2013/0184813 A1 | 7/2013 | Quadri et al. |
| 2013/0190861 A1 | 7/2013 | Chau et al. |
| 2013/0211508 A1* | 8/2013 | Lane ............... A61F 2/2403 623/2.11 |
| 2013/0253635 A1 | 9/2013 | Straubinger et al. |
| 2013/0253642 A1 | 9/2013 | Brecker |
| 2013/0261737 A1 | 10/2013 | Costello |
| 2013/0304200 A1 | 11/2013 | McLean et al. |
| 2013/0310928 A1* | 11/2013 | Morriss ............ A61F 2/2418 623/2.12 |
| 2013/0345786 A1 | 12/2013 | Behan |
| 2014/0005764 A1 | 1/2014 | Schroeder |
| 2014/0018912 A1 | 1/2014 | Delaloye et al. |
| 2014/0039611 A1 | 2/2014 | Lane et al. |
| 2014/0046427 A1 | 2/2014 | Michalak |
| 2014/0052237 A1 | 2/2014 | Lane et al. |
| 2014/0052242 A1 | 2/2014 | Revuelta et al. |
| 2014/0067054 A1 | 3/2014 | Chau et al. |
| 2014/0088685 A1 | 3/2014 | Yevzlin et al. |
| 2014/0100651 A1 | 4/2014 | Kheradvar et al. |
| 2014/0100653 A1 | 4/2014 | Savage et al. |
| 2014/0142694 A1 | 5/2014 | Tabor et al. |
| 2014/0155990 A1 | 6/2014 | Nyuli et al. |
| 2014/0163668 A1* | 6/2014 | Rafiee ................. 623/2.11 |
| 2014/0172083 A1 | 6/2014 | Bruchman et al. |
| 2014/0172085 A1 | 6/2014 | Quadri et al. |
| 2014/0172086 A1 | 6/2014 | Quadri et al. |
| 2014/0194981 A1 | 7/2014 | Menk et al. |
| 2014/0194983 A1 | 7/2014 | Kovalsky et al. |
| 2014/0214153 A1 | 7/2014 | Ottma et al. |
| 2014/0214154 A1 | 7/2014 | Nguyen et al. |
| 2014/0214155 A1 | 7/2014 | Kelley |
| 2014/0214159 A1 | 7/2014 | Vidlund et al. |
| 2014/0214160 A1 | 7/2014 | Naor |
| 2014/0222136 A1 | 8/2014 | Geist et al. |
| 2014/0222139 A1 | 8/2014 | Nguyen et al. |
| 2014/0222142 A1 | 8/2014 | Kovalsky et al. |
| 2014/0236288 A1 | 8/2014 | Lambrecht et al. |
| 2014/0243966 A1 | 8/2014 | Garde et al. |
| 2014/0257467 A1 | 9/2014 | Lane et al. |
| 2014/0257476 A1 | 9/2014 | Montorfano et al. |
| 2014/0277390 A1 | 9/2014 | Ratz et al. |
| 2014/0277402 A1 | 9/2014 | Essinger et al. |
| 2014/0277422 A1 | 9/2014 | Ratz et al. |
| 2014/0277423 A1 | 9/2014 | Alkhatib et al. |
| 2014/0277427 A1 | 9/2014 | Ratz et al. |
| 2014/0296973 A1 | 10/2014 | Bergheim et al. |
| 2014/0296975 A1 | 10/2014 | Tegels et al. |
| 2014/0303719 A1 | 10/2014 | Cox et al. |
| 2014/0309728 A1 | 10/2014 | Dehdashtian et al. |
| 2014/0309731 A1 | 10/2014 | Quadri et al. |
| 2014/0309732 A1 | 10/2014 | Solem |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0330371 A1 | 11/2014 | Gloss et al. |
| 2014/0330372 A1 | 11/2014 | Weston et al. |
| 2014/0331475 A1 | 11/2014 | Duffy et al. |
| 2014/0336754 A1 | 11/2014 | Gurskis et al. |
| 2014/0343669 A1 | 11/2014 | Lane et al. |
| 2014/0343670 A1 | 11/2014 | Bakis et al. |
| 2014/0343671 A1 | 11/2014 | Yohanan et al. |
| 2014/0350666 A1 | 11/2014 | Righini |
| 2014/0350668 A1 | 11/2014 | Delaloye et al. |
| 2014/0358221 A1 | 12/2014 | Ho et al. |
| 2014/0364939 A1 | 12/2014 | Deshmukh et al. |
| 2014/0364943 A1 | 12/2014 | Conklin |
| 2014/0364944 A1 | 12/2014 | Lutter et al. |
| 2014/0371842 A1 | 12/2014 | Marquez et al. |
| 2014/0371845 A1 | 12/2014 | Tuval et al. |
| 2014/0371847 A1 | 12/2014 | Madrid et al. |
| 2014/0371848 A1 | 12/2014 | Murray, III et al. |
| 2014/0379067 A1 | 12/2014 | Nguyen et al. |
| 2014/0379068 A1 | 12/2014 | Thielen et al. |
| 2014/0379077 A1 | 12/2014 | Tuval et al. |
| 2015/0005873 A1 | 1/2015 | Chang et al. |
| 2015/0012085 A1 | 1/2015 | Salahieh et al. |
| 2015/0018938 A1 | 1/2015 | Von Segesser et al. |
| 2015/0018944 A1 | 1/2015 | O'Connell et al. |
| 2015/0032153 A1 | 1/2015 | Quadri et al. |
| 2015/0066140 A1 | 3/2015 | Quadri |
| 2015/0081009 A1 | 3/2015 | Quadri |
| 2015/0142100 A1* | 5/2015 | Morriss ............ A61F 2/2418 623/2.4 |
| 2015/0142103 A1 | 5/2015 | Vidlund |
| 2015/0148731 A1 | 5/2015 | McNamara et al. |
| 2015/0157458 A1 | 6/2015 | Thambar et al. |
| 2015/0196390 A1 | 7/2015 | Ma et al. |

FOREIGN PATENT DOCUMENTS

| | | |
|---|---|---|
| DE | 3128704 | 2/1983 |
| DE | 10 2006 052 564 | 12/2007 |
| EP | 0 657 147 | 6/1995 |
| EP | 1 47 996 B1 | 11/2004 |
| EP | 1 255 510 B1 | 4/2007 |
| EP | 1 772 104 A2 | 4/2007 |
| GB | 1 264 471 | 2/1972 |
| GB | 1315 844 | 5/1973 |
| GB | 2245495 | 1/1992 |
| GB | 2 398 245 | 8/2004 |
| JP | 2002-540889 | 12/2002 |
| JP | 2008-541865 | 11/2008 |
| WO | WO 97/49355 | 12/1997 |
| WO | WO 00/53104 | 9/2000 |
| WO | WO 00/61034 | 10/2000 |
| WO | WO 01/35861 | 5/2001 |
| WO | WO 01/35870 | 5/2001 |
| WO | WO 01/72239 | 10/2001 |
| WO | WO 02/36048 | 5/2002 |
| WO | WO 03/092554 | 11/2003 |
| WO | WO 03/028522 | 1/2004 |
| WO | WO 2004/014257 | 2/2004 |
| WO | WO 2004/014474 | 2/2004 |
| WO | WO 2004/058097 | 7/2004 |
| WO | WO 2005/011534 | 2/2005 |
| WO | WO 2005/041810 | 5/2005 |
| WO | WO 2005/087140 | 9/2005 |
| WO | WO 2006/070372 | 7/2006 |
| WO | WO 2006/085304 | 8/2006 |
| WO | WO 2006/089236 | 8/2006 |
| WO | WO 2006/127765 | 11/2006 |
| WO | WO 2007/025028 | 3/2007 |
| WO | WO 2007/034488 | 3/2007 |
| WO | WO 2007/058857 | 5/2007 |
| WO | WO 2007/123658 | 11/2007 |
| WO | WO 2007/134290 | 11/2007 |
| WO | WO 2008/005535 | 1/2008 |
| WO | WO 2008/013915 | 1/2008 |
| WO | WO 2008/070797 | 6/2008 |
| WO | WO 2008/091515 | 7/2008 |
| WO | WO 2008/103722 | 8/2008 |
| WO | WO 2008/150529 | 12/2008 |
| WO | WO 2009/026563 | 2/2009 |
| WO | WO 2009/033469 | 3/2009 |
| WO | WO 2009/045331 | 4/2009 |
| WO | WO 2009/052188 | 4/2009 |
| WO | WO 2009/053497 | 4/2009 |
| WO | WO 2009/091509 | 7/2009 |
| WO | WO 2009/094500 | 7/2009 |
| WO | WO 2009/134701 | 11/2009 |
| WO | WO 2009/137359 | 11/2009 |
| WO | WO 2009/155561 | 12/2009 |
| WO | WO 2010/008549 | 1/2010 |
| WO | WO 2010/037141 | 4/2010 |
| WO | WO 2010/040009 | 4/2010 |
| WO | WO 2010/057262 | 5/2010 |
| WO | WO 2010/098857 | 9/2010 |
| WO | WO 2009/149462 | 1/2011 |

(56) References Cited

FOREIGN PATENT DOCUMENTS

| WO | WO 2010/138853 | 2/2011 |
|---|---|---|
| WO | WO 2011/025945 | 3/2011 |
| WO | WO 2011/137531 | 11/2011 |
| WO | WO 2011/109801 | 1/2012 |
| WO | WO 2011/109813 | 1/2012 |
| WO | WO 2012/035279 | 3/2012 |
| WO | WO 2012/162228 | 11/2012 |
| WO | WO 2012/177942 | 12/2012 |
| WO | WO 2013/028387 | 2/2013 |
| WO | WO 2013/012801 | 4/2013 |
| WO | WO 2013/086413 | 6/2013 |

OTHER PUBLICATIONS

U.S. Appl. No. 14/186,989, filed Feb. 21, 2014, Quadri et al.
U.S. Appl. No. 14/197,639, filed Mar. 5, 2014, Ratz et al.
U.S. Appl. No. 14/197,690, filed Mar. 5, 2014, Ratz et al.
U.S. Appl. No. 29,484,001, filed Mar. 5, 2014, Pesce et al.
CardiAQ Valve Technologies, "Innovations in Heart Valve Therapy," In3 San Francisco, Jun. 18, 2008, PowerPoint presentation in 19 slides.
European Extended Search Report, re EP Application No. 14159271.7, dated Jul. 23, 2014.
European Extended Search Report, re EP Application No. 14159378.0, dated Jul. 24, 2014.
European Extended Search Report, re EP Application No. 14159090.1, dated Jul. 22, 2014.
U.S. Appl. No. 61/331,799, filed May 5, 2010, Lane et al.
U.S. Appl. No. 61/393,860, filed Oct. 15, 2010, Lane et al.
U.S. Appl. No. 61/414,879, filed Nov. 17, 2010, Lane et al.
U.S. Appl. No. 14/598,568, filed Jan. 16, 2015, Quadri et al.
U.S. Appl. No. 14/628,034, filed Feb. 20, 2015, Rabito et al.
U.S. Appl. No. 14/702,233, filed May 1, 2015, Arshad et al.
U.S. Appl. No. 14/716,507, filed May 19, 2015, Ratz et al.
Neovasc Surgical Products, "Neovasc Surgical Products: An Operating Division of Neovasc Inc.," dated Apr. 2009.
Kronemyer, Bob: "CardiAQ Valve Technologies: Percutaneous Mitral Valve Replacement," Start Up—Windhover Review of Emerging Medical Ventures, vol. 14, Issue No. 6, Jun. 2009, pp. 48-49.
Bavaria, Joseph E. M.D.: "CardiAQ Valve Technologies: Transcatheter Mitral Valve Implantation," Sep. 21, 2009.
Ostrovsky, Gene: "Transcatheter Mitral Valve Implantation Technology from CardiAQ," medGadget, Jan. 15, 2010, available at: http://www.medgadget.com/2010/01/transcatheter_mitral_valve_implantation_technology_from_cardiaq.html.
"Company Overview," Jun. 25, 2009 at TVT.
"Update," Applicant believes this may have been presented on Jun. 6, 2010 at TVT.
Banai, Shmuel, et al., Tiara: A Novel Catheter-Based Mitral Valve Bioprosthesis, Initial Experiments and Short-Term Pre-Clinical Results, Journal of the American College of Cardiology, vol. 60, No. 15, 2012. Applicant believes that this may have been available online as early as Sep. 12, 2012.
Berreklouw, Eric, MD, PhD, et al., "Sutureless Mitral Valve Replacement With Bioprostheses and Nitinol Attachment Rings: Feasibility in Acute Pig Experiments," The Journal of Thoracic and Cardiovascular Surgery, vol. 142, No. 2, Aug. 2011 in 7 pages, Applicant believes this may have been available online as early as Feb. 4, 2011.
Boudjemline, Younes, MD, et al., "Steps Toward the Percutaneous Replacement of Atrioventricular Valves," JACC, vol. 46, No. 2, Jul. 19, 2005:360-5.
Brinkman, William T., MD, et al., Transcatheter Cardiac Valve Interventions, Surg Clin N Am 89 (2009) 951-966, Applicant believes this may have been available as early as Aug. 2009.
Chiam, Paul T.L., et al., "Percutaneous Transcatheter Aortic Valve Implantation: Assessing Results, Judging Outcomes, and Planning Trials," JACC: Cardiovascular Interventions, The American College of Cardiology Foundation, vol. 1, No. 4, Aug. 2008:341-50.
Condado, Jose Antonio, et al., "Percutaneous Treatment of Heart Valves," Rev Esp Cardio. 2006;59(12):1225-31, Applicant believes this may have been available as early as Dec. 2006.
Engager System, Precise Valve Positioning, Transcatheter Aortic Valve Implantation System, Transcatheter Aortic Valve Replacement—TAVR I Medtronic Engager, http://www.medtronic-engager.com/home/transcatheter-aortic-valve-repl., 2014 Medtronic, Inc. in 2 pages. Applicant believes this may have been available online as early as Aug. 25, 2013.
Fanning, Jonathon P., et al., "Transcatheter Aortic Valve Implantation (TAVI): Valve Design and Evolution," International Journal of Cardiology 168 (2013) 1822-1831, Applicant believes this may have been available as early as Aug. 20, 2013.
Fitzgerald, Peter J. M.D., "Tomorrow's Technology: Percutaneous Mitral Valve Replacement, Chordal Shortening, and Beyond," Transcatheter Valve Therapies (TVT) Conference. Seattle, WA. Applicant believes this may have been available as early as Jun. 7, 2010.
Gillespie, Matthew J., MD, et al., "Sutureless Mitral Valve Replacement: Initial Steps Toward a Percutaneous Procedure," Ann Thorac Surg. Aug. 2013; 96(2).
Grube, Eberhard, MD, et al., "Percutaneous Implantation of the CoreValve Self-Expanding Valve Prosthesis in High-Risk Patients With Aortic Valve Disease, The Siegburg First-in-Man Study" Journal of the American Heart Association, 2006; 114:1616-1624, originally published online Oct. 2, 2006.
JenaValve Technology, "The JenaValve—The Prosthesis", 2011 JenaValve Technology in 1 page.
Karimi, Houshang, MD, et al., "Percutaneous Valve Therapies," SIS 2007 Yearbook, Chapter 11, pp. 1-11.
Lauten, Alexander, et al., "Experimental Evaluation of the JenaClip Transcatheter Aortic Valve," Catheterization and Cardiovascular Interventions 74:514-519, published online May 11, 2009, Applicant believes this may have been available online as early as Apr. 27, 2009.
Leon, Martin B., MD, et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages, Applicant believes this may have been available as early as the Summer of 2006.
Lozonschi, Lucian, MD, et al., "Transapical Mitral Valved Stent Implantation," Ann Thorac Surg 2008;86:745-8 in 4 pages, Applicant believes this may have been available as early as Sep. 2008.
Lutter, G., et al.: "Transcatheter Mitral Valve Replacement—Early Animal Results," Universitätsklinikum, Schleswig-Holstein, unknown publication date.
Lutter, Georg, et al., "Off-Pump Transapical Mitral Valve Replacement," European Journal of Cardio-thoracic Surgery 36 (2009) 124-128, Applicant believes this may have been available as early as Apr. 25, 2009.
Ma, Liang, et al., "Double-Crowned Valved Stents for Off-Pump Mitral Valve Replacement," European Journal of Cardio-thoracic Surgery 28 (2005) 194-199, Applicant believes this may have been available as early as Aug. 2005.
Mack, Michael, M.D., "Antegrade Transcatheter Mitral valve Implantation: A Short-term Experience in Swine Model," Applicant believes this may have been presented on May 2011 at TVT.
Mack, Michael, M.D., "Antegrade Transcatheter Mitral valve Implantation: On-Going Experience in Swine Model," Applicant believes this may have been presented on Nov. 2011 at TCT.
Masson, Jean-Bernard, et al., "Percutaneous Treatment of Mitral Regurgitation," Circulation: Cardiovascular Interventions, 2:140-146, Applicant believes this may have been available as early as Apr. 14, 2009.
Ostrovsky, Gene, "A Trial of Zenith Fenestrated AAA Endovascular Graft Goes on," medGadget, Aug. 1, 2008, available at: :http://www.medgadget.com/2008/08/a_trial_of_zenith_fenestrated_aaa_endovascular_graft_goes_on.html.

(56) References Cited

OTHER PUBLICATIONS

Pluth, James R., M.D., et al., "Aortic and Mitral Valve Replacement with Cloth-Covered Braunwald-Cutter Prosthesis, A Three-Year Follow-up," The Annals of Thoracic Surgery, vol. 20, No. 3, Sep. 1975, pp. 239-248.
Quadri, Arshad M.D., "Transcatheter Mitral Valve Implantation (TMVI) (An Acute In Vivo Study)," Applicant believes this may have been presented on Sep. 22, 2010 at TCT.
Ratz, J. Brent, "In3 Company Overview," Jun. 24, 2009.
Ratz, J. Brent, "LSI EMT Spotlight," May 15, 2009.
Ruiz, Carlos E., "Overview of Novel Transcatheter Valve Technologies," Applicant believes this may have been presented on May 27, 2010 at EuroPCR.
Seidel, Wolfgang, et al., "A Mitral Valve Prosthesis and a Study of Thrombosis on Heart Valves in Dogs," JSR—vol. II, No. 3—May 1962, submitted for publication Oct. 9, 1961.
Sondergaard, Lars, et al., "Transcatheter Mitral Valve Implantation: CardiAQ™," Applicant believes this may have been presented at EuroPCR May 2013.
Sondergaard, Lars, et al., "Transcatheter Mitral Valve Implantation: CardiAQ™," Applicant believes this may have been presented at TCT Oct. 2013.
Spillner, J. et al., "New Sutureless 'Atrial-Mitral-Valve Prosthesis' For Minimally Invasive Mitral Valve Therapy," Textile Research Journal, 2010, in 7 pages, Applicant believes this may have been available as early as Aug. 9, 2010.
Vu, Duc-Thang, MD, et al., "Novel Sutureless Mitral Valve Implantation Method Involving a Bayonet Insertion and Release Mechanism: A Proof of Concept Study in Pigs," The Journal of Thoracic and Cardiovascular Surgery, vol. 143, No. 4, 985-988, Apr. 2012, Applicant believes this may have been available online as early as Feb. 11, 2012.
Walther, Thomas et al., "Transapical Approach for Sutureless Stent-Fixed Aortic Valve Implantation: Experimental Results," European Journal of Cardio-thoracic Surgery 29 (2006) 703-708, Applicant believes this may have been available as early as May 2006.
Webb, John G., et al., "Transcatheter Aortic Valve Implantation: The Evolution of Prostheses, Delivery Systems and Approaches," Archives of Cardiovascular Disease (2012) 105, 153-159, Applicant believes this may have been available as early as Mar. 16, 2012.
Banai et al.: "Transapical Mitral Implantation of the Tiara Bioprosthesis," JACC: Cardiovascular Interventions, vol. 7, No. 2, Feb. 2014:154-62.
Bavaria, Joseph E. M.D. et al.: "Transcatheter Mitral Valve Implantation: The Future Gold Standard for MR?," Applicant requests the Examiner to consider this reference to be prior art as of Dec. 2010.
BioSpace, "CardiAQ Valve Technologies (CVT) Reports Cardiovascular Medicine Milestone: First-In-Humannonsurgical Percutaneous Implantation of a Bioprosthetic Mitral Heart Valve," Jun. 14, 2012, p. 1, http://www.biospace.com/News/cardiaq-valve-technologies-cvt-reports/263900.
Businesswire.com, "CardiAQ Valve Technologies (CVT) Discloses Successful Results of Acute In Vivo Study of Its Novel Transcatheter Mitral Valve Implantation (TMVI) System," Sep. 28, 2009.
Businesswire.com, CardiAQ Valve Technologies, "CardiAQ Valve Technologies ("CVT") to disclose data during 'EuroPCR 2010' about the world's first successful in vivo transcatheter delivery of a mitral heart valve implant," Irvine, California, May 20, 2010.
CardiAQ Valve Technologies Company Fact Sheet 2009.

Diagnostic and Interventional Cardiology, "Neovasc Announces Publication of Tiara Transcatheter Mitral Valve Preclinical Data in JACC," Sep. 18, 2012, p. 1, http://www.dicardiology.com/content/neovasc-announces-publication-tiara-transcatheter-mitral-valve-preclinical-data-jacc.
Diagnostic and Interventional Cardiology, "Neovasc Announces Successful Human Implant of Tiara Transcatheter Mitral Valve," Feb. 18, 2014, p. 1, <http://www.dicardiology.com/article/neovasc-announces-successful-human-implant-tiara-transcatheter-mitral-valve>.
Diagnostic and Interventional Cardiology, "Neovasc Receives First U.S. Patent for its Tiara Transcatheter Mitral Valve Replacement Technology," Nov. 15, 2013, p. 1, <http://www.dicardiology.com/content/neovasc-receives-first-us-patent-its-tiara-transcatheter-mitral- valve-replacement-technology>.
Feldman, Ted, MD. "Prospects for Percutaneous Valve Therapies," Circulation 2007;116:2866-2877. Applicant believes that this may be available as early as Dec. 11, 2007.
Grube, E. et al, "Percutaneous aortic valve replacement for severe aortic stenosis in high-risk patients using the second- and current third-generation self-expanding CoreValve prosthesis: device success and 30-day clinical outcome." J Am Coll Cardiol. Jul. 3, 2007;50(1):69-76. Epub Jun. 6, 2007.
Horvath et al.: "Transapical Aortic Valve Replacement under Real-time Magnetic Resonance Imaging Guidance: Experimental Results with Balloon-Expandable and Self-Expanding Stents," http://www.ncbi.nlm.nih.gov/pmc/articles/PMC3038190/. Jun. 2011.
Mack, Michael M.D., "Advantages and Limitations of Surgical Mitral Valve Replacement; Lessons for the Transcatheter Approach," Applicant believes this may have been available as early as Jun. 7, 2010. Applicant believes this may have been presented at the Texas Cardiovascular Innovative Ventures (TCIV) Conference in Dallas, TX on Dec. 8, 2010.
Neovasc corporate presentation, Oct. 2009, available at http://www.neovasc.com/investors/documents/Neovasc-Corporate-Presentation-October-2009.pdf.
Piazza, Nicoló, MD, et al., "Anatomy of the Aortic Valvar Complex and Its Implications for Transcatheter Implantation of the Aortic Valve," Contemporary Reviews in Interventional Cardiology, Circ. Cardiovasc. Intervent., 2008;1:74-81, Applicant believes this may have been available as early as Aug. 2008.
Ratz, J. Brent et al., "Any experiences making an expandable stent frame?" Arch-Pub.com, Architecture Forums: Modeling, Multiple forum postings from Feb. 3, 2009 to Feb. 4, 2009, http://www.arch-pub.com.
Ratz, J. Brent et al., "Fabric, Skin, Cloth expansion . . . best approach?," AREA by Autodesk, 3ds Max: Modeling, Forum postings from Feb. 18, 2009 to Feb. 19, 2009, http://area.autodesk.com.
Ratz, J. Brent et al., "Isolating Interpolation," Arch-Pub.com, Architecture Forums: Animation and Rigging, Forum postings from Feb. 9, 2009 to Feb. 10, 2009, http://www.arch-pub.com.
Treede et al.: "Transapical transcatheter aortic valve implantation using the JenaValve™ system: acute and 30-day results of the multicentre CE-mark study." http://ejcts.oxfordjournals.org/content/41/6/e131.long. Apr. 16, 2012.
Van Mieghem, et al., "Anatomy of the Mitral Valvular Complez and Its Implications for Transcatheter Interventions for Mitral Regurgitation," J. Am. Coll. Cardiol., 56:617-626 (Aug. 17, 2010).
Wayback Machine, Neovasc Ostial Products Overview, https://web.archive.org/web/20090930050359/https://www.neovasc.com/vascular-products/ostialproducts/default.php, indicated as archived on Sep. 30, 2008.

* cited by examiner

PROSTHESIS FOR ATRAUMATICALLY GRASPING INTRALUMENAL TISSUE AND METHODS OF DELIVERY

CROSS-REFERENCE TO RELATED APPLICATIONS

This application claims the benefit of priority to U.S. Provisional Appl. No. 61/782,707, filed Mar. 14, 2013, 61/789,783, filed Mar. 15, 2013, and 61/798,115 filed Mar. 15, 2013. The entire contents of the above applications are hereby incorporated by reference and made a part of this specification. Any and all priority claims identified in the Application Data Sheet, or any correction thereto, are hereby incorporated by reference under 37 CFR 1.57.

BACKGROUND OF THE INVENTION

Field of the Invention

Certain embodiments disclosed herein relate generally to prostheses for implantation within a lumen or body cavity. In particular, certain embodiments relate to expandable prostheses such as replacement heart valves, such as for the mitral valve, that are configured to atraumatically grasp intralumenal tissue.

Description of the Related Art

Human heart valves, which include the aortic, pulmonary, mitral and tricuspid valves, function essentially as one-way valves operating in synchronization with the pumping heart. The valves allow blood to flow downstream, but block blood from flowing upstream. Diseased heart valves exhibit impairments such as narrowing of the valve or regurgitation, which inhibit the valves' ability to control blood flow. Such impairments reduce the heart's blood-pumping efficiency and can be a debilitating and life threatening condition. For example, valve insufficiency can lead to conditions such as heart hypertrophy and dilation of the ventricle. Thus, extensive efforts have been made to develop methods and apparatuses to repair or replace impaired heart valves.

Prostheses exist to correct problems associated with impaired heart valves. For example, mechanical and tissue-based heart valve prostheses can be used to replace impaired native heart valves. More recently, substantial effort has been dedicated to developing replacement heart valves, particularly tissue-based replacement heart valves that can be delivered with less trauma to the patient than through open heart surgery. Replacement valves are being designed to be delivered through minimally invasive procedures and even percutaneous procedures. Such replacement valves often include a tissue-based valve body that is connected to an expandable frame that is then delivered to the native valve's annulus.

Development of prostheses including but not limited to replacement heart valves that can be compacted for delivery and then controllably expanded for controlled placement has proven to be particularly challenging. An additional challenge relates to the ability of such prostheses to be secured relative to intralumenal tissue, e.g., tissue within any body lumen or cavity, in an atraumatic manner. These replacement valves are often intended to at least partially block blood flow. However, a problem occurs when blood flows around the valve on the outside of the prosthesis. For example, in the context of replacement heart valves, paravalvular leakage has proven particularly challenging.

SUMMARY OF THE INVENTION

Embodiments of the present disclosure are directed to a prosthesis, such as but not limited to a replacement heart valve. In some embodiments a prosthesis can comprise an expandable frame, a plurality of distal anchors and a plurality of proximal anchors. The anchors can extend outwardly from the frame. The frame can be configured to radially expand and contract for deployment within the body cavity. When the frame is in an expanded configuration, the proximal anchors can extend a significant distance away from the exterior of the frame, such as a length of about one-half or more the diameter of the frame. In some embodiments, at least some of the anchors comprise a loop that forms an atraumatic end of a corresponding anchor. In some embodiments, an outer skirt may be positioned annularly around an exterior of the expandable frame and be connected to some of the anchors to create an axial barrier to fluid flow exterior to the frame when deployed within the body cavity.

Further embodiments are directed to methods of delivering a prosthesis, e.g. a replacement heart valve, methods of securing a prosthesis to intralumenal tissue, and methods of using a prosthesis to create a barrier to fluid flow exterior to the prosthesis (e.g., to prevent paravalvular leakage).

In some embodiments, a prosthesis can be configured to grasp intralumenal tissue when deployed within a body cavity. The prosthesis can comprise an expandable frame, a plurality of proximal anchors connected to the frame, and a plurality of distal anchors connected to the frame. The expandable frame can comprise a proximal end and a distal end and a longitudinal axis extending therethrough, the frame configured to collapse radially for delivery and to expand radially upon deployment. The plurality of proximal anchors can be expandable to a configuration wherein a portion of each of the proximal anchors extends generally distally and an end of each of the proximal anchors is positioned radially outward from the frame. The plurality of distal anchors can be expandable to a configuration wherein a portion of each of the distal anchors extends generally proximally and an end of each of the distal anchors is positioned radially outward from the frame. Expansion of the frame from a first at least partially collapsed size to a second expanded size can cause the ends of the proximal anchors and the ends of the distal anchors to draw closer together. At least some of the plurality of proximal anchors can be configured to expand to a radial distance from a central longitudinal axis of the frame that is about 150% or more of a radius of the frame when the frame is in an expanded configuration.

BRIEF DESCRIPTION OF THE DRAWINGS

These and other features, aspects and advantages are described below with reference to the drawings, which are intended to illustrate but not to limit the invention. In the drawings, like reference characters denote corresponding features consistently throughout similar embodiments.

DETAILED DESCRIPTION OF THE PREFERRED EMBODIMENTS

The present specification and drawings provide aspects and features of the disclosure in the context of several embodiments of prostheses, replacement heart valves, delivery devices and methods that are configured for use in the vasculature of a patient, such as for replacement of natural heart valves in a patient. These embodiments may be discussed in connection with replacing specific valves such as the patient's aortic or mitral valve. However, it is to be understood that the features and concepts discussed herein can be applied to products other than heart valve implants. For example, the controlled positioning, deployment, and securing features described herein can be applied to medical implants, for example other types of expandable prostheses, for use elsewhere in the body, such as within a vein, or the like. In addition, particular features of a valve, delivery device, etc. should not be taken as limiting, and features of any one embodiment discussed herein can be combined with features of other embodiments as desired and when appropriate.

Figure 1:
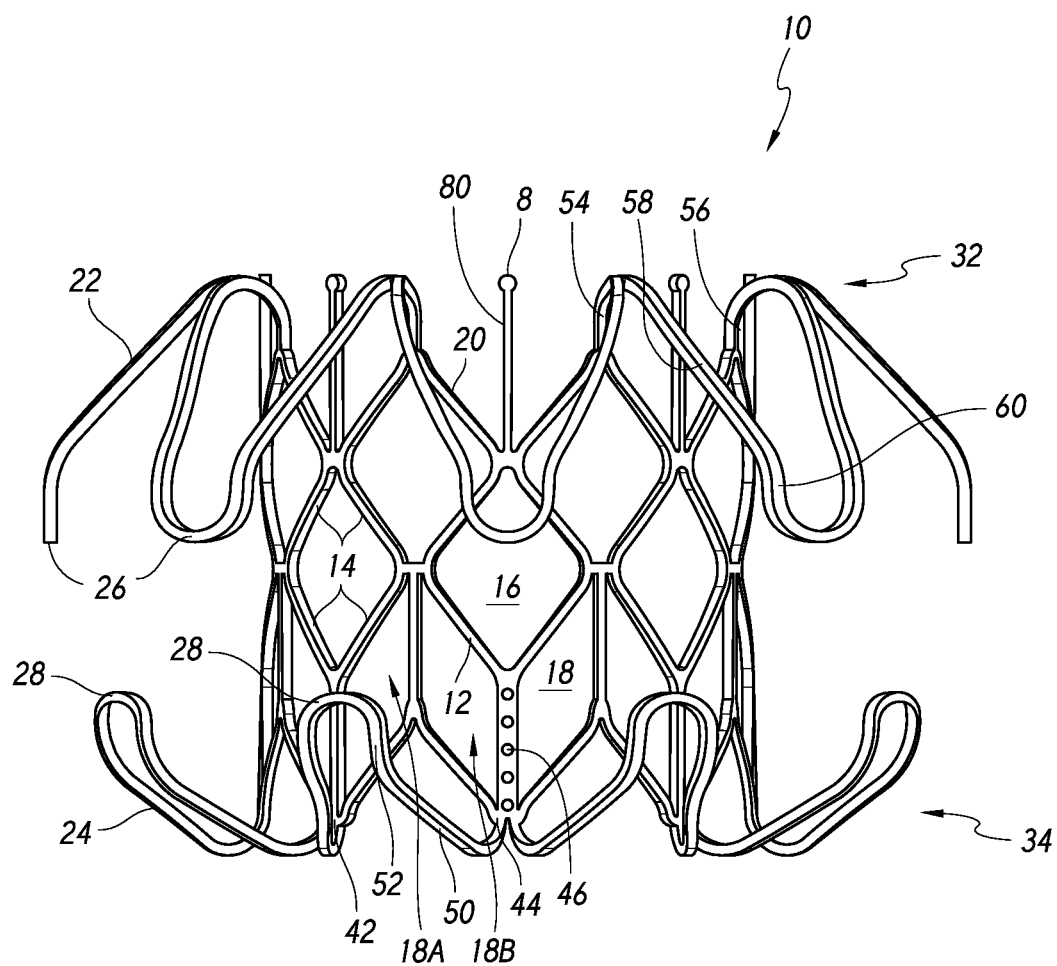
FIG. 1 is a side view of a frame for a prosthesis.

With initial reference to FIG. 1, an embodiment of a prosthesis 10 is shown. The illustrated prosthesis 10 includes a frame 20 that may be self-expanding or balloon expandable. The frame 20 can include a proximal end 32, a distal end 34 and proximal 22 and distal 24 anchors. The anchors can allow the frame to engage a native valve annulus or other tissue to be implanted at a target location. The prosthesis 10 can include one or more of a valve 60, an outer skirt 30, and a valve skirt 70 as will be described in more detail below. The valve 60 can be designed to replace a damaged or diseased native heart valve such as a mitral valve; though it will be understood that a replacement valve is not required as part of the prosthesis.

The prosthesis can be a replacement heart valve similar to that and including features similar to those disclosed in U.S. Provisional Appl. No. 61/782,707, filed Mar. 14, 2013 and 61/789,783 filed Mar. 15, 2013, U.S. Pat. No. 8,403,983 and U.S. Publication Nos. 2010/0298931, 2011/0313515 and 2012/0078353 the entireties of each of which are hereby incorporated by reference and made a part of this specification. This is inclusive of the entire disclosure and is not in any way limited to the disclosure of the replacement heart valve.

The frame 20 can be made of many different materials, but is preferably made from metal. In some embodiments, the frame 20 can be made from a shape memory material, such as nitinol. A wire frame or a metal tube can be used to make the frame. The wire frame of a metal tube can be cut or etched to remove all but the desired metal skeleton. In some embodiments a metal tube is laser cut in a repeating pattern to form the frame. The flat pattern can be cut from a metal tube and then the tube can be bent and expanded to the shape shown in FIG. 1. The frame 20 can further be expanded and/or compressed and/or otherwise worked to have the desired shape or shapes, such as for introduction and implantation.

As shown, the frame when in an expanded configuration, such as in a fully expanded configuration, has a cylindrical or slightly cylindrical shape, where a middle portion is substantially similar in shape and size as the proximal 32 and distal 34 ends. The frame can be a substantially cylindrical shape with the same or substantially the constant cross-sectional dimension or diameter from the proximal end to the distal end. The cylindrical shape of the frame, in combination with the anchors described below, can advantageously allow the frame to float within a native valve while the anchors engage a native valve annulus or other body cavity and spacing the inlet and outlet of the frame away from the heart or vessel wall. This can help reduce undesired contact between the prosthesis and the heart or vessel, such as the ventricular wall of the heart. The prosthesis 10 and frame 20 may be similar to the replacement heart valves and associated frames disclosed in U.S. Provisional Appl. No. 61/782,707, filed Mar. 14, 2013 and 61/789,783 filed Mar. 15, 2013, U.S. Pat. No. 8,403,983 and U.S. Publication Nos. 2010/0298931 and 2011/0313515 the entireties of each of which are hereby incorporated by reference and made a part of this specification. This is inclusive of the entire disclosure and is not in any way limited to the disclosure of the replacement heart valves and associated frames.

A number of struts collectively make up the frame 20. FIG. 1 illustrates the frame in an expanded configuration with a number of longitudinal struts 12 and undulating struts 14, with cells 16, 18 defined by the open spaces between the struts. The longitudinal struts may be arranged so that they are parallel or generally or substantially parallel to a longitudinal axis of the frame. The longitudinal axis of the frame may be defined as the central axis that extends through the center of the frame between the proximal 32 and distal 34 ends. Any number of configurations of struts can be used, such as the rings of undulating struts shown forming chevrons and diamonds, but also ovals, curves, and various other shapes. The illustrated embodiment includes two rows of diamond-shaped cells 16 at the top or adjacent the proximal end and then a row of sideways diamond-shaped cells 18 at the bottom or near the distal end. These sideways diamond-shapes are made of two longitudinal struts 12 that are offset from one another, or one is higher than the other, and then an undulating strut 14 connects the longitudinal struts 12 at the top and bottom of the cell. The sideways diamond-shapes alternate between sides as to which side is higher and which is lower. So a first sideways diamond-shaped cell 18A has a low left side and a high right side, and a second sideways diamond-shaped 18B had a high left side and a low right side, where the high right side of cell 18A shares the same longitudinal strut 12 as the high left side of cell 18B.

Some of the struts can include one or more eyelet 46. As illustrated, a plurality of eyelets, here five, are located along one of the longitudinal struts 12 as part of the sideways diamond-shaped cells. One or more eyelets can be positioned in other locations along the frame and/or anchors. The eyelets 46 may be used to attach features such as the valve 60, outer skirt 30, and/or valve skirt 70 to the frame 20.

The frame 20 as illustrated is foreshortening. The foreshortening can be defined by the frame 20 and the positioning of various types of struts along the frame 20. When the frame is radially collapsed or compacted, the struts 14 become more parallel with respect to the longitudinal axis of the frame, causing cells 16 and 18 to collapse, causing an outer diameter of the frame to decrease and the longitudinal length of the frame to increase. As the frame moves from a compacted position to an expanded position, the cells 16 and 18 widen sideways and the longitudinal length of the frame can decrease. It will be appreciated while in some embodiments the entire length of the frame 20 is foreshortening, in other embodiments such as embodiments of the prostheses described in the patents and applications incorporated by reference herein, only a portion of the frame is foreshortening.

Foreshortening of the frame 20 can be used to engage and secure the prosthesis to intralumenal tissue in a body cavity, for example tissue at or adjacent a native valve, such as a native valve annulus and/or leaflets. Opposing anchors 22, 24 can be constructed on the frame 20 so that portions of the anchors, such as tips or ends 26, 28, move closer together as the frame foreshortens. As one example, this can allow the anchors 22, 24 to grasp tissue on opposite sides of the native mitral annulus to thereby secure the prosthesis at the mitral valve.

The anchors 22, 24 and anchor tips 26, 28 can be located anywhere along the frame 20 just so long as at least one of the anchors is either connected to a foreshortening portion or a foreshortening portion is positioned between the anchors so that a portion of the anchors will be move closer together with expansion of the frame. As shown in FIG. 1, the foreshortening portion extends the entire or substantially the entire length of the frame.

Preferably, each of the anchors 22, 24 is positioned or extends generally radially outwardly from the frame 20 so that the anchor tips 26, 28 are generally spaced away or radially outward from the rest of the frame 20. For example, the anchor tips may be located radially outward from the middle portion of the frame, with the tips 26 and 28 being axially spaced from one another. In some embodiments, all or part of the structure connected to the anchor tip and extending radially from the frame, including one or more rings and/or struts, can be considered part of the anchor. The anchors can include a base located on the anchor on a side opposite the tip. The base can be for example where the anchor begins to extend from or away from the frame 20.

For example, the distal anchors 24 are shown having looped anchors. Each looped anchor has a first base 42 and a second base 44 connected to the frame, wherein the first and second bases are at the distal-most corners of adjacent cells. Alternatively, the first and second bases may be located at adjacent corners of the same cell, or at opposite corners of the same cell if for example the cells adjacent the distal end of the frame have the same configuration as the cells shown in FIG. 1 at the proximal end of the frame. The distal anchors 24 extend generally distally away from the frame and are bent near the base 42 to extend radially outward away from the frame along a first segment 50. Then the anchor is bent to point proximally or generally proximally along a second segment 52 ending in the tip 28. The tips 28 of the distal anchors may be curved or arcuate atraumatic tips. The ends of the distal anchors can extend proximally and be parallel or substantially parallel with the longitudinal axis of the frame, or they may extend generally proximally but still radially outwardly inclined or at an acute angle relative to the longitudinal axis of the frame. The distal anchor 24 then repeats this configuration in reverse towards the second base 44 such that the two sides of the looped anchor are mirror images of one another.

In addition, as illustrated in FIG. 1, adjacent distal anchors share one strut so that each distal anchor is directly adjacent another distal anchor. In other embodiments, distal anchors can be spaced apart, for example with at least a cell 18 or two cells 18 located between the distal anchors. It will be understood that the distal anchors can have other configurations such as described in the applications included in the appendix and that the distal anchors may not be symmetrical.

The proximal anchors 22 are shown having looped anchors of a similar shape and configuration as the distal anchors 24. It can be seen that each proximal anchor extends from or near the proximal end of the frame at bases 54 and 56 located on adjacent proximal-most corners of cells 16. In the embodiment illustrated in FIG. 1, the proximal anchors are longer than the distal anchors, and as such, the proximal anchors may extend further away from the frame. As shown the anchors extend proximally at the bases 54, 56 and are then bent to segment 58 which extends radially outwardly away from the frame in a generally distal direction. Then the proximal anchor is bent to point distally or generally distally along a second segment 60 ending in the tip 26. The tips 26 of the proximal anchors may be curved or arcuate atraumatic tips. The ends of the proximal anchors can extend distally and be parallel or substantially parallel with the longitudinal axis of the frame, or they may extend generally distally but still radially outwardly inclined or at an acute angle relative to the longitudinal axis of the frame. Another embodiment, described below with respect to FIG. 6, has the ends of the proximal anchors becoming perpendicular to the longitudinal axis of the frame.

In addition, adjacent proximal anchors can share the same base where the anchors are bent outward from the frame, or may be considered to extend from the same corner on cell 16. In other embodiments, proximal anchors can be spaced apart so that there is at least a ½ cell or one cell located between the proximal anchors. It will be understood that the proximal anchors can have other configurations such as described in the applications included in the appendix and that the proximal anchors may not be symmetrical. As illustrated in FIG. 1, between the bases 54 and 56 of each proximal anchor, there may also be located a longitudinally extending strut 80 extending proximally, e.g. from the proximal-most corner of a cell 16 in the second row of cells from the proximal end. These struts 80 may terminate at their proximal ends in an enlarged portion such as a tab 8 that may facilitate holding or retaining the proximal end of the frame, such as in a delivery system as described below.

In some embodiments, in an expanded state such as shown in FIG. 1, at least some of the proximal anchors can extend to a radial distance from an exterior surface of the frame that is ½ (or about ½) or more of the expanded diameter of the frame. In some embodiments, all of the proximal anchors extend at least to this radial distance. In even further embodiments, all of the proximal and distal anchors extend at least to this radial distance. In other embodiments, the radial distance of one or more of the ends of the anchors from a central longitudinal axis passing through the middle of the frame may be 150% (or about 150%) or more, 180% (or about 180%) or more, 200% (or about 200%) or more, 220% (or about 220%) or more, or 250% (or about 250%) or more of the radius of the frame when the frame and the anchors are in expanded configurations. For example, if the radius of the frame is 16 mm and a proximal anchor end is spaced 9 mm from the exterior of the frame, that proximal anchor extends 25 mm from the central longitudinal axis of the frame, and is 156.25% of the radius of the frame.

In some embodiments the diameter of the frame 20 may be in the range of 20-40 mm (or about 20 to about 40 mm), more preferably 25-35 mm (or about 25 to about 35 mm) when expanded. The outermost tip diameter may be greater than the frame diameter as described above and may be in the range of 40-60 mm (or about 40 to about 60 mm), and in some embodiments may be about 50 mm when the frame diameter is about 30 mm. In some embodiments the length of the prosthesis, from proximal to distal end, when compressed, is between 20-40 mm (or about 20 to about 40 mm), more preferably 25 to 30 mm (or about 25 to about 30 mm), for example about 29 mm. When expanded, the prosthesis may have a length between 15 to 20 mm (or about 15 to 20 mm), more preferably 17 to 18 mm (or about 17 to about 18 mm).

The distal anchors 24 can be positioned to be not as far radially outward as the proximal anchors, and the tips 28 may be positioned radially inward of the tips 26. As described further below, such a configuration may be advantageous in positioning and securing the prosthesis in a mitral valve or other body location. In some embodiments, as illustrated in FIG. 1, the ends or tips 26 of the proximal anchors 22 are positioned further radially outward from the frame 20 than the ends of tips 28 distal anchors 24 when the frame and the anchors are in an expanded configuration, e.g., when they are fully expanded. In other embodiments, the distal anchors and proximal anchors can be positioned at the same radial outward dimension, or the distal anchors may even be positioned further outward than the proximal anchors. In further embodiments, some of the proximal anchors (or distal anchors) may extend to a first radial distance, and others of the proximal anchors (or distal anchors) may extend to a second radial distance, where the first radial distance is greater than the second radial distance. The distal anchors in FIG. 1 are shown to be circumferentially staggered with respect to the proximal anchors, meaning that the tips 26 of the proximal anchors are not aligned, and are circumferentially in between the tips 28 of the distal anchors. In other embodiments, the tips 26 and 28 may be circumferentially aligned.

It will be understood that the anchors can have various other configurations. In some embodiments, each of the anchors can extend radially outwardly from the frame at an anchor base and terminate at an anchor tip. The anchors can be connected to the frame at one of many different locations including apices, junctions, other parts of struts, etc. The anchors can comprise first, second, third, or more spaced apart bending stages along the length of each anchor. The anchors can also extend either distally or proximally before and/or after one or more of the bending stages. A portion of the anchor may extend with the frame before or after any bending stages. As shown, the anchors 22, 24 may comprise loops as described above, having a curved or arcuate atraumatic tip to minimize damage to body tissue. Further details that may be incorporated and/or interchanged with the features described herein are disclosed in U.S. Provisional Appl. No. 61/782,707, filed Mar. 14, 2013 and 61/789,783 filed Mar. 15, 2013, U.S. Pat. No. 8,403,983 and U.S. Publication Nos. 2010/0298931, 2011/0313515 and 2012/0078353, incorporated by reference herein.

In one embodiment the prosthesis has nine distal anchors and nine proximal anchors. Any number of proximal and distal anchors may be used. In other embodiments, instead of a 1:1 correspondence between anchors, other ratios, such as a 9:6 or a 9:3 correspondence between the anchors, are possible.

With respect to the number of cells and rows of cells, when there are nine proximal anchors and nine distal anchors, there may be two rows of nine cells 16 each. The cells in the second row can share struts 14 from the first row. A third row at the distal end can have a different cell configuration with sideways diamonds as illustrated in FIG. 1, and can for example have eighteen cells 18, with each cell 18 sharing a strut from a cell in the second row. In other embodiments, the third row can include cells similar in shape to cells 16 in the first and second rows. In another embodiment, a frame may have one or more rows of diamond-shaped cells, where the number of cells per row is 12 or some other number.

The anchor tips 26 and 28 as described above advantageously provide atraumatic surfaces that may be used to grasp intralumenal tissue without causing unnecessary or undesired trauma to tissue. For example, the proximal anchors tips 26 and distal anchor tips 28 may form flat, substantially flat, curved or other non-sharp surfaces to allow the tips to engage and/or grasp tissue, without necessarily piercing or puncturing through tissue. A looped end or looped anchor may assist the frame in not getting caught up on structures at or near the treatment location. For example, each loop can be configured so that when the frame is deployed in-situ and the anchors expand away from the frame, the movement of each loop from a delivered position to a deployed position avoids getting caught on the papillary muscles.

Figure 6:
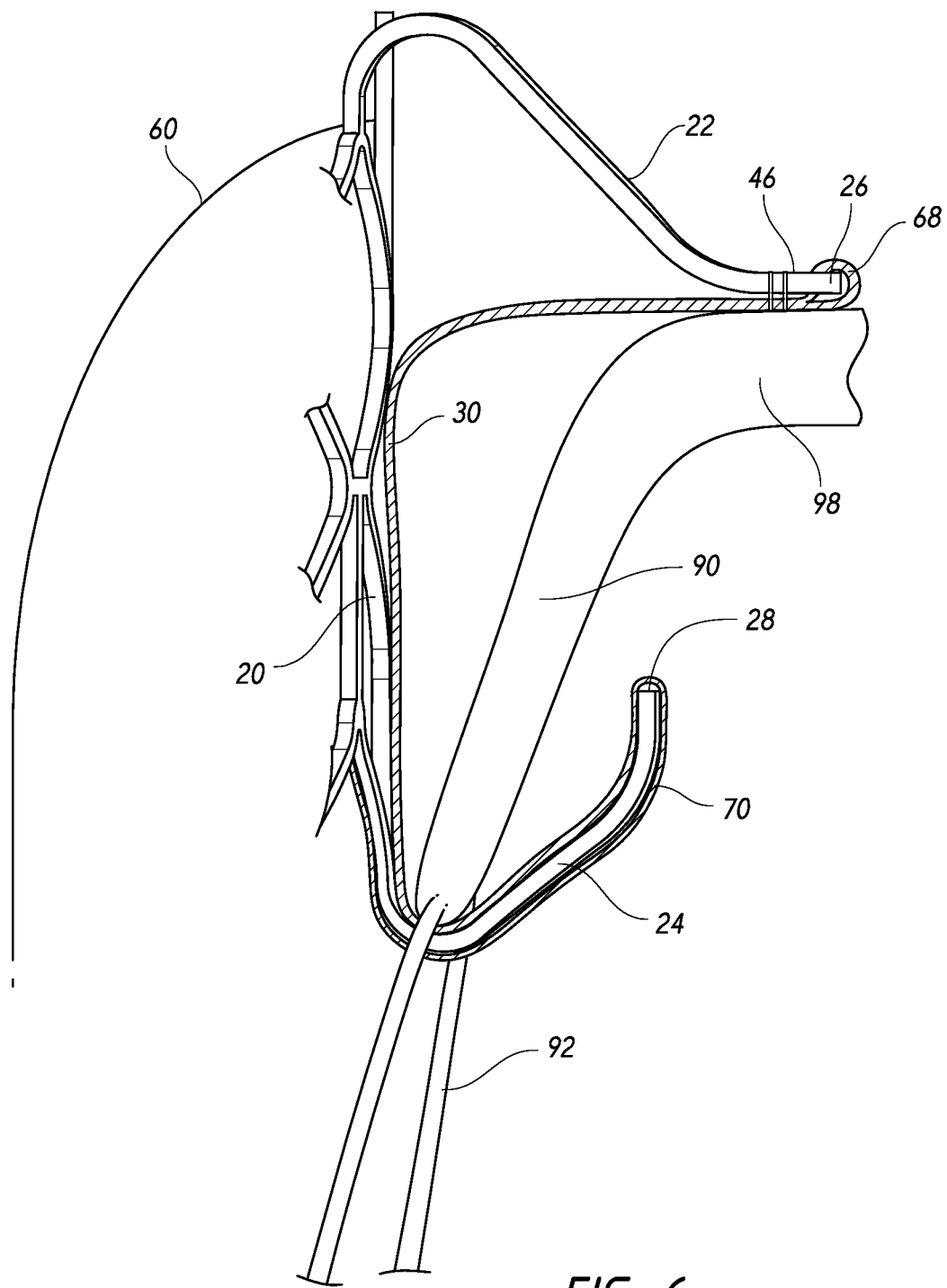
FIG. 6 is a detail schematic representation of the prosthesis positioned within the heart of FIG. 5.

The prosthesis 10 may include a valve 60 as can be seen in schematically in FIG. 6. The valve 60 can be a replacement heart valve which includes a plurality of valve leaflets. The plurality of valve leaflets can function in a manner similar to the natural mitral valve, or to other valves in the vascular system. The plurality of valve leaflets can open in a first position and then engage one another to close the valve in a second position. The plurality of valve leaflets can be made to function as a one way valve such that flow in one direction opens the valve and flow in a second direction opposite the first direction closes the valve. The replacement heart valve 60 can be constructed so as to open naturally with the beating of the heart. For example, the plurality of valve leaflets can open during diastole and close during systole.

Figure 2:
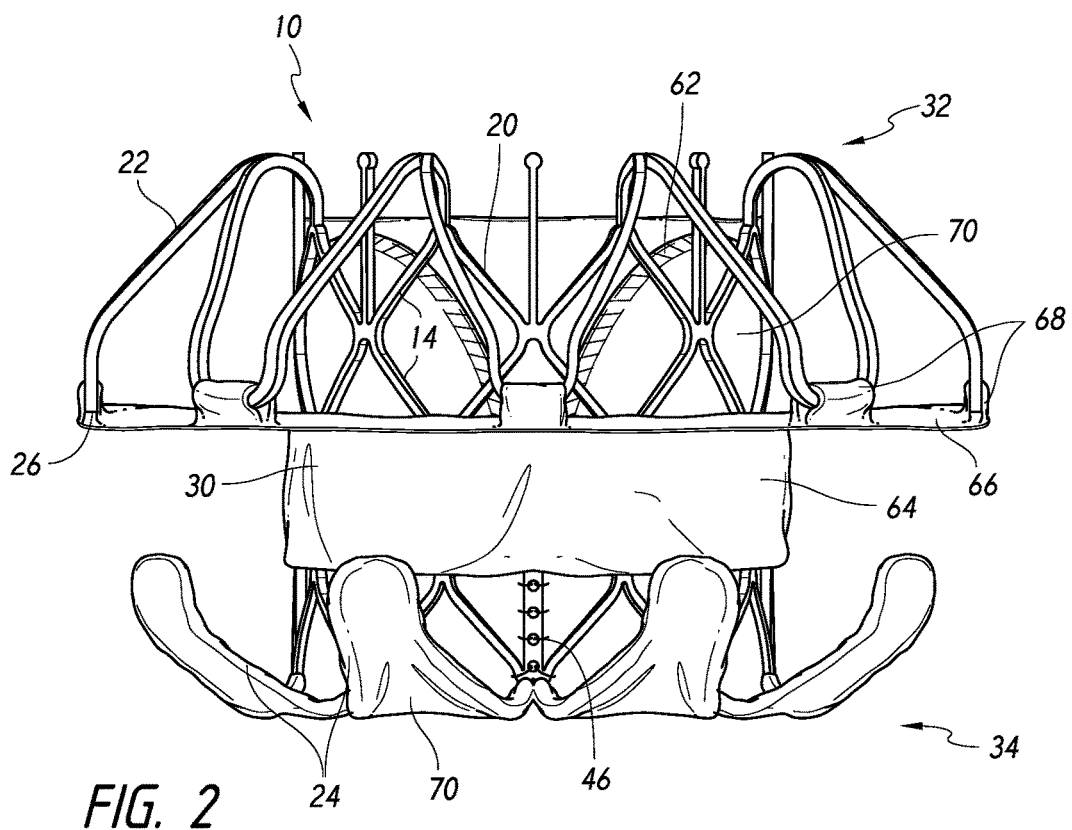
FIG. 2 is an embodiment of a prosthesis configured as a replacement heart valve.

In some embodiments, the leaflets can be coupled to a valve skirt 70. For example, FIG. 2 shows a seam 62 where the proximal ends of the leaflets can be connected to the valve skirt 70.

The valve skirt 70 can be used to at least partially control how fluid flows through and/or around the valve 60. The valve skirt 70 can surround at least a portion of the valve and be connected to the valve leaflets. In some embodiments, the valve skirt 70 can form an inner wall connected to and positioned within the frame 20. For example the skirt 70 can connect to the frame at the eyelets 46, such as by stitching. The skirt may also be attached directing to the struts, typically also by stitching. The valve skirt 70 can also be made to move with the foreshortening portion of the frame 20.

The valve skirt 70 can extend the length of the frame 20 or it can extend along only part of the length of the frame 20. In some embodiments, the ends of the heart valve 60 can coincide with ends of the valve skirt 70. In addition, one or more of the ends of the frame 20 can coincide with the ends of the valve skirt 70. In the illustrated embodiment of FIG. 2, the proximal end of the valve skirt 70 is positioned proximally from the proximal end of the heart valve 60 as indicated by the seam 62. The valve skirt 70 can not only extend to the distal end of the frame 20 but can also extend to the outside of the frame and is shown attached to and extending to the tip 28 of each distal anchor 24. As shown, the skirt 70 is sewn to each distal anchor.

Other shapes and configurations can also be used for the valve 60 and valve skirt 70. In some embodiments, the valve skirt 70 may extend along the length of the leaflets, but is not connected to them. In the illustrated embodiments, the valve skirt 70 is attached to the frame 20 and the leaflets are attached to the valve skirt 70, such as at the seam 62 in FIG. 2.

The valve skirt 70 can be constructed in multiple different ways. The valve skirt 70 can be made a layer of resilient material, such as knit polyester or another stretchable or flexible fabric. In some embodiments, the valve skirt 70 is made from a material that is more flexible than the valve leaflet material. The distal and/or proximal end of the skirt 70 can be straight, curved, or have any other desired configuration. For example, the valve skirt 70 is shown with a straight proximal end at the proximal end 32 of the frame. In other embodiments the skirt distal end can be patterned to generally correspond to the undulations at one end of the frame 20. The valve skirt 70 can be formed of one piece or multiple pieces. For example, the valve skirt 70 attached to the valve 60 can be one piece and then each distal anchor can be covered by a separate piece of material of the valve skirt 70. It is to be understood that other configurations of the valve skirt 70 can also be employed. For example, the anchors may remain uncovered, or only a portion may be covered.

In another embodiment of the valve skirt 70, the end can extend past the frame and can be wrapped around it. Thus, the valve skirt 70 can extend from the inside of the frame 20 to the outside of the frame. The skirt can extend completely around the frame for ¼, ⅓, ½, or more of the length of the distal anchors. Such an embodiment is shown and described with respect to FIGS. 7A-7B of Provisional Appl. No. 61/782,707. The skirt 70 can also cover the distal anchors 24 as is shown in FIGS. 7A and 7B of Provisional Appl. No. 61/782,707 and in FIG. 2 herein. The skirt can be a one piece skirt, but it will be understood that the skirt can be made of multiple pieces.

The valve skirt 70, and particularly portions that cover the distal anchors 24, can beneficially be used to help prevent leakage of blood flow around the heart valve. In addition, the skirt can encourage tissue in-growth between the skirt and the natural tissue. This may further help to prevent leakage of blood flow around the heart valve.

Continuing to look to FIG. 2, an outer skirt or apron 30 is shown that may also form part of the prosthesis 10. FIG. 2 shows the outer skirt 30 attached to the frame 20 at the tips 26 of the proximal anchors. The outer skirt 30 can have a portion shaped to correspond generally with the shape of an outer portion of the frame 20. For example, a first portion 64 of the outer skirt 30 can have a cylindrical or generally cylindrical shape with an inner diameter that substantially corresponds in size to, or may be larger or slightly larger than, an outer diameter of the frame 20. The outer skirt 30 can have a second portion 66 with an annular shape that extends away from the first portion 64 to an outer border with a diameter larger than the diameter of the first portion. As illustrated in FIG. 2, the second portion 66 is shown flaring outward from the first portion 64 and extending generally perpendicularly from the first portion 64. Thus, the illustrated second portion forms an annular ring comprising a proximal edge and a distal edge, wherein a diameter of the proximal edge is larger than a diameter of the distal edge.

The outer skirt 30 can attach to the frame, and more preferably attach to the anchors, in one of many different ways. The outer skirt 30 can be sewn to the frame and/or valve skirt. The outer skirt 30 can also be wrapped around a portion of the frame and then sewn to itself. In the embodiment illustrated in FIG. 2, the second portion 66 is attached to the proximal anchors 22. For example, a plurality of circumferentially spaced tabs 68 extending radially outward from the proximal edge of the second portion 66 can be used to attach the outer skirt 30 to the proximal anchors. The tabs 68 can be wrapped around the tip 26 (e.g., through the loop) of a proximal anchor and connected to the second portion. The tabs 68 themselves may also form sleeves that are configured to surround at least a portion of the proximal anchors. In some embodiments, the proximal anchors 22 can include eyelets that may be used to secure the skirt to the anchor. The tab 68 can be attached to the eyelet 46, for example by stitching.

In one embodiment, the outer skirt 30 is only attached to the frame via the proximal anchors, and the first portion 64 remains unattached to any portion of the frame or any anchors. In another embodiment, the outer skirt is both attached to the proximal anchors and to the middle portion of the frame. As illustrated in FIG. 2, the second portion 66 attached to the anchors extends inwardly from the proximal anchors 22. The first portion 64 then extends distally from the second portion 66 and terminates in a distal edge, which may be free or which may attach to the middle portion of the frame 20 or the skirt 70. In other embodiments, the first portion 64 may also be attached to portions of the frame and/or the distal anchors. In some embodiments, the distal edge of the skirt 30 may be spaced radially outward from the frame when the frame is in an expanded configuration. In addition, the distal edge of the skirt 30 may extend to the distal end of the frame, or it may be spaced proximally therefrom as illustrated in FIG. 2.

In some embodiments, the outer skirt 30 can attach to the frame at a distal end of the skirt, or at some other location and then curve up and out towards the proximal anchors. Thus, the outer skirt may not have a distinct first portion and second portion. In still other embodiments, the outer skirt may extend along a substantial portion of the frame. Additional examples of outer skirt features that may be incorporated and/or interchanged with the features described herein are found in U.S. Provisional Application No. 61/789,783 filed Mar. 15, 2013 incorporated by reference herein.

Figure 3:
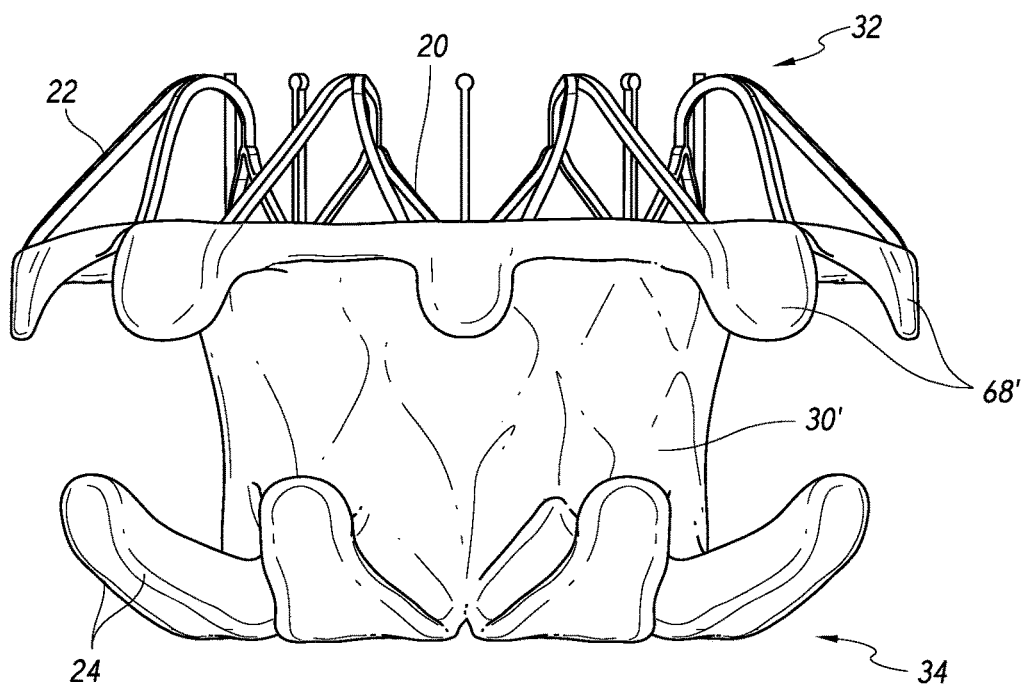
FIG. 3 is an embodiment of a prosthesis configured as a replacement heart valve.
Figure 4:
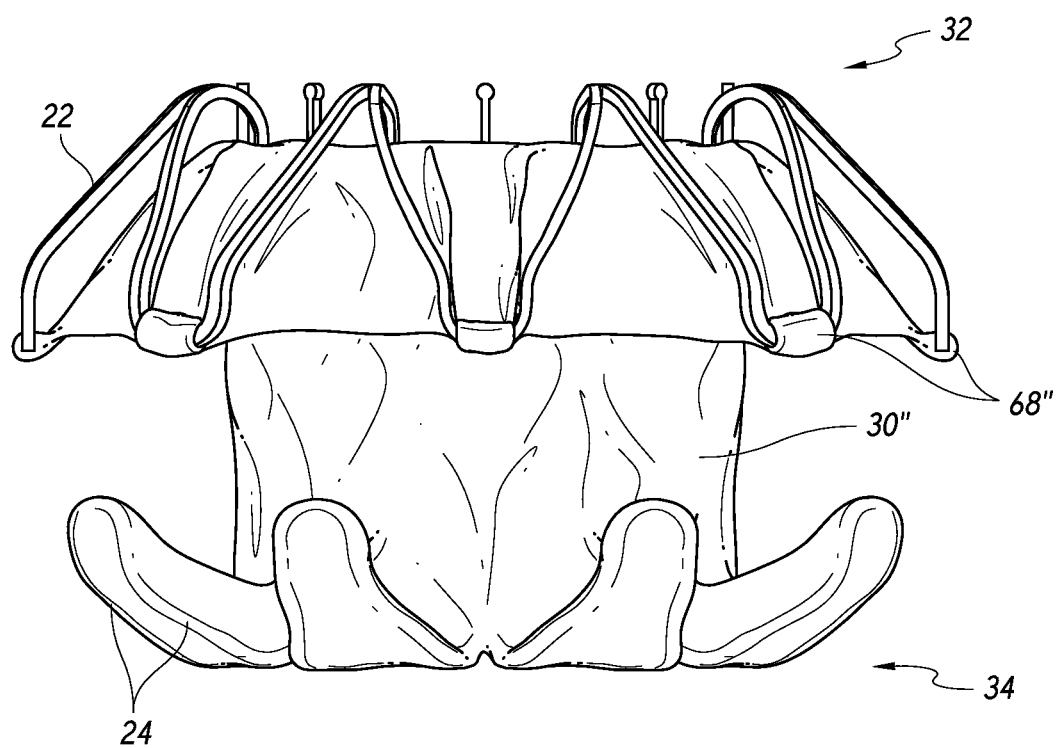
FIG. 4 is an embodiment of a prosthesis configured as a replacement heart valve.

FIGS. 3 and 4 show additional embodiments of the outer skirt 30', 30". In FIG. 3, the outer skirt 30' extends along a substantial part of the frame and extends between proximal and distal anchors. The outer skirt 30' in this embodiment may be one single piece, or may be formed from multiple pieces stitched or otherwise connected together. The tabs 68' may form sleeves that are configured to surround at least a portion of the proximal anchors to attach the outer skirt to the proximal anchors. As shown in one embodiment, proximal portions of the proximal anchors remain uncovered by the outer skirt 30'. The outer skirt 30' at the proximal anchors can form an annular ring similar to the second portion 66 of FIG. 2 and can form a substantially cylindrical portion similar to the first portion 64 of FIG. 2. The distal end of the outer skirt 30' can attach and/or cover the distal anchors 24. In some embodiments, the distal end of the outer skirt 30' extends to the distal anchors 24 but does not cover or connect to them. In addition, a valve skirt 70 may also be used which may create some overlap of skirts in some embodiments.

In FIG. 4 the outer skirt 30" is shown attached to the distal ends of the proximal anchors 22 with tabs 68". The outer skirt 30" then extends proximally to essentially the base of the proximal anchor. From that point, the outer skirt extends distally towards the distal end. Again the outer skirt may or may not attach to the distal anchors. In the illustrated embodiment of FIG. 4, the outer skirt 30" wraps around each of the distal anchors.

Turning now to FIG. 6, a detail view of an embodiments is shown where the proximal anchors 22 can include eyelets 46 that may be used to secure the skirt to the anchor. In this embodiment, the proximal anchor has an end 26 that instead of extending generally distally, it extends generally radially outwardly, and as illustrated extends in a direction perpendicular or substantially perpendicular to the longitudinal axis of the frame. The tab 68 can be attached to the eyelet 46, for example by stitching. As shown, the eyelet 46 is positioned at the end of the anchor, but it will be understood that it can be spaced proximally from the end. In some embodiments, the proximal anchors can be looped anchors or have a looped end. A small tab can be passed through the looped anchor or looped end and connected to the skirt to form a loop on the skirt. Further, the outer skirt 30 may attach directly to the eyelets 46 without the need for tabs 68.

In some embodiments, the outer skirt 30 can be part of, or connected to, the valve skirt 70, such as being connected to the valve skirt 70 at or near the distal end 34 of the frame.

The outer skirt 30 can be constructed in multiple different ways and may be made of similar material to the valve skirt 70. The outer skirt 30 can be made of a layer of resilient material, such as knit polyester or another stretchable or flexible fabric. In some embodiments, the outer skirt 30 is made from a material that is more flexible than the valve leaflet material. The distal and/or proximal end of the outer skirt 30 can be straight, curved, or have any other desired configuration. The outer skirt 30 can be formed of one piece or multiple pieces. For example, the outer skirt 30 attached to the frame 20 can be one piece and then each proximal anchor 22 can be covered by a separate piece of material of the outer skirt 30. It is to be understood that other configurations of the outer skirt 30 can also be employed. For example, the anchors may remain uncovered, or only a portion may be covered.

The outer skirt 30 can beneficially prevent axial flow of fluid around an exterior of the prosthesis. For example, with the outer skirt 30 be positioned annularly around an exterior of the expandable frame and secured to at least some of the plurality of proximal anchors, the outer skirt creates an axial barrier to fluid flow exterior to the frame when deployed within a body cavity. In addition, the skirt can encourage tissue in-growth between the skirt and the natural tissue. This may further help to prevent leakage of blood flow around the heart valve.

In one embodiment, the outer skirt 30 can be used to help prevent leakage of blood flow around a heart valve, such as a mitral valve, when the prosthesis is placed in a native heart valve. For example, the outer skirt 30 can engage an atrial side of the mitral valve. The proximal anchors can also engage the mitral valve forcing the outer skirt 30 into close contact with the valve to block flow from passing through the mitral valve from outside of the frame.

Figure 5:
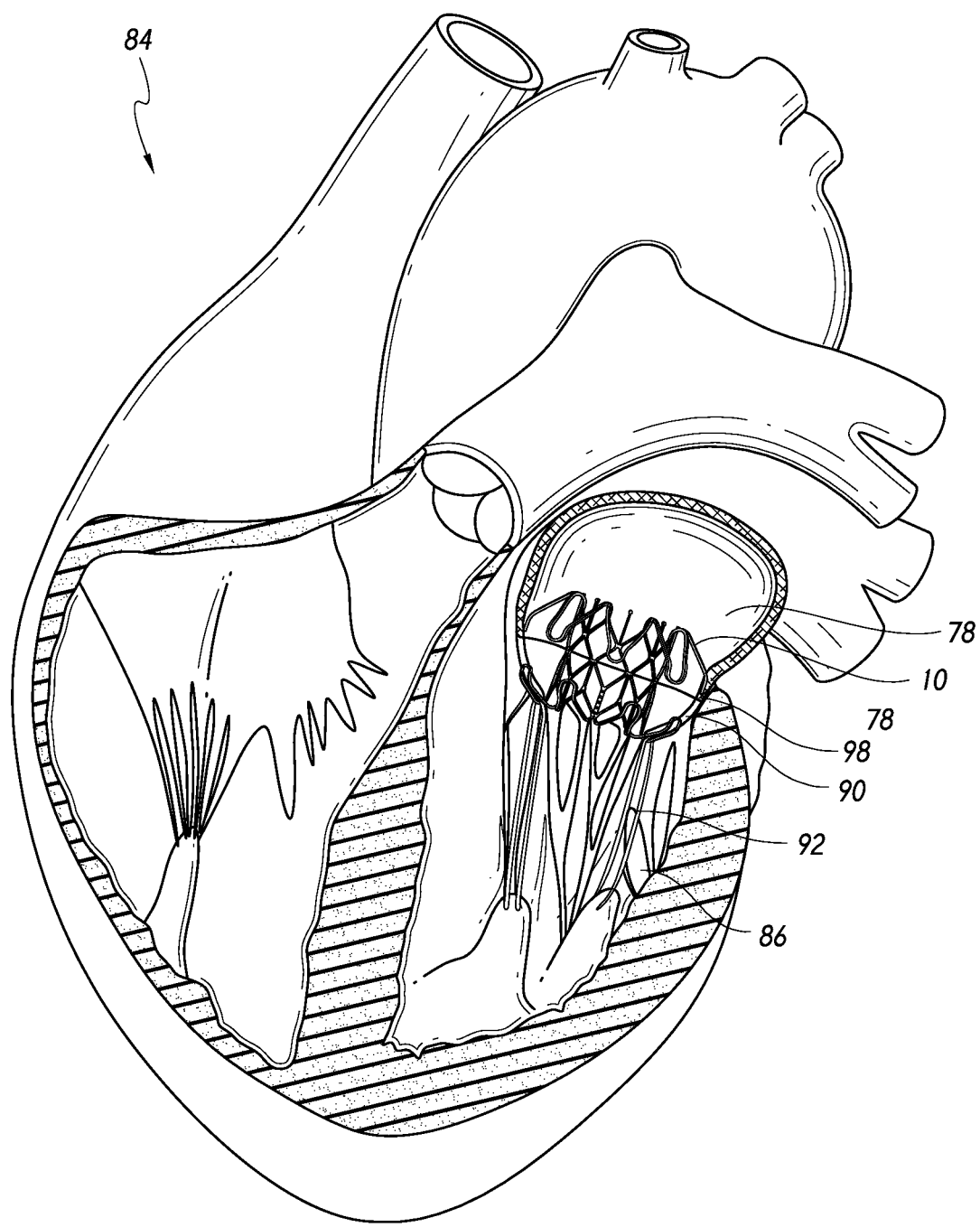
FIG. 5 is a schematic representation of a prosthesis positioned within the heart.

In preferred embodiments, the prostheses 10 in the form of a replacement heart such as described above may be deployed into a heart valve annulus. The prosthesis 10 may be delivered into the mitral valve in a radially compacted or collapsed configuration and positioned when compacted so that the anchor tips 26, 28 of the opposing anchors 22, 24 are disposed on opposite sides of the native annulus 98 as shown in FIGS. 5 and 6. In FIG. 5, the valve 60 and skirts are not shown for ease of illustration. As the replacement heart valve 10 is expanded, the opposing anchors expand outward away from the frame are may be drawn closer together due to foreshortening of the frame. The anchors may grasp tissue on opposite sides of the native annulus 98 and securely hold the replacement heart valve 10 in position. As such, the replacement heart valve 10 can be held securely in position without requiring a substantial radial force against the native annulus. Because the anchor tips are preferably atraumatic, the grasping or engaging of tissue by the prosthesis minimizes damage to the native tissue. The prosthesis can be deployed into a heart valve or otherwise deployed in manners similar to those described with respect to a replacement heart valve in U.S. Publication Nos. 2010/0298931 and 2012/0078353 the entireties of each of which are hereby incorporated by reference and made a part of this specification.

FIGS. 5 and 6 show a schematic representation of the replacement heart valve 10 installed in a human heart 84. The heart is shown in cross-section, and represents typical anatomy, including a left atrium 78 and left ventricle 86. The left atrium 78 and left ventricle 86 communicate with one another through a mitral annulus 98. Also shown schematically is a native anterior mitral leaflet 90 having chordae tendineae 92 that connect a downstream end of the anterior mitral leaflet 90 and to the left ventricle 86. FIG. 6 shows an enlarged view of a slightly different prosthesis implanted at the native mitral annulus.

In one preferred embodiment, a method is provided of delivering a replacement valve to a native mitral valve and atraumatically securing the replacement valve relative to the native mitral valve annulus 98. The replacement valve can be mounted on a delivery device and delivered to the native mitral valve annulus while the replacement valve is in a radially compacted state. The replacement valve may be positioned so that the ends or tips of the distal anchors are on a ventricular side of the native leaflets 90 beyond a location where chordae tendineae 92 connect to free ends of the native leaflets. At least a portion of the replacement valve can be released from the delivery device to thereby expand the distal anchors radially outwardly. At this time the distal anchors may extend between at least some of the chordae. The distal anchors (along with the frame) can be moved toward the ventricular side of the native valve annulus with the distal anchors extending between at least some of the chordae tendineae to provide tension on the chordae tendineae. With tension provided on the chordae tendineae, the replacement valve can be further released from the delivery device to thereby expand the proximal anchors radially outwardly. The proximal anchors upon further release of the replacement valve from the delivery device can move into engagement with tissue on an atrial side of the native valve annulus, such as with the atrial side of the native valve annulus.

The method just described may utilize any of the prostheses herein described, including those described in the patent and applications incorporated by reference. The illustrated prosthesis where the ends of the distal anchors are not positioned as far out radially as the ends of the proximal anchors when the frame is expanded can beneficially be used in this method. Thus, the distal anchors may have a suitable length for extending between and providing tension on the chordae tendineae, but need not and may in some embodiments not engage tissue with the tips 28, such as shown in FIG. 6. Thus, in some embodiments some or all of the distal anchors remain spaced from tissue on the ventricular side of the native valve annulus after delivery and expansion. The interaction between the distal anchors and the chordae tendineae may therefore be sufficient to secure the distal end of the prosthesis, while the engagement of the proximal anchors with tissue on the atrial side of the native valve annulus will help further secure and orient the prosthesis As illustrated in FIGS. 5 and 6, the distal anchors may comprise loops, such as any of the looped structures previously described. The proximal and/or distal anchors may also be covered with a resilient material such as described above for the outer skirt 30 and valve skirt 70 that promotes tissue growth with adjacent body tissue. Such material may also be useful to prevent paravalvular leakage. The atraumatic distal anchors may advantageously prevent snagging of the prosthesis on internal structures, such as the papillary muscles.

When the prosthesis is in an expanded configuration within the native mitral heart valve, the engagement of the proximal anchors 22 with tissue on the atrial side of the native mitral valve causes at least a portion of the outer skirt 30 to also engage the tissue on the atrial side of the native mitral valve. A portion of the outer skirt extends distally from the proximal anchors toward the ventricle. Because the diameter of the outer skirt decreases to a size of close or the same in dimension as the frame, the outer skirt form a barrier to blood flow around the outside or external to the frame. The outer skirt 30 can be forced against the outside of the frame 20 by the native leaflets. Where the native leaflets do not force the outer skirt 30 against the frame, or where the contact is not as strong, the outer skirt 30 is still present to block, or impede blood flow. It will be understood that having multiple contact points between the native valve and the outer skirt can allow the outer skirt to securely cover areas where there are fewer contacts between the two. As described above, the outer skirt may also promote tissue growth with tissue that it contacts.

In addition, due to the preferred outer dimension of the anchors relative to the diameter or radius of the frame in some embodiments, when the frame is radially expanded such that the proximal and/or distal anchors engage tissue at or around the native mitral valve annulus, the frame may move reciprocally in an axial direction relative to the native mitral valve annulus in a constrained floating manner. The one or more of the anchors 22, 24 can be made to flex to provide this reciprocal movement; for example, around the bends between the segments 50, 56 and the base of the anchors. The frame does not exert a significant amount of radial force to the native mitral valve annulus or adjacent tissues, and the frame is primarily secured with the anchors. When in use, the frame may then move relative to the anchor ends as the heart is beating.

The embodiments described in FIGS. 1-6 above may have further advantages. As illustrated in FIG. 1, some embodiments have only 3 rows of cells or less, which makes the prosthesis longitudinally shorter and therefore easier to navigate when collapsed through tortuous pathways (e.g., percutaneously). Because of the dimensions of the anchors relative to the size of the frame, the frame itself may be made relatively smaller, which also helps facilitate a lower profile for the prosthesis helpful for delivery and implantation. Moreover, having a prosthesis that can "float" within a native annulus may be usable for a wider variety of patient anatomies, as one or a fewer number of radial sizes of the frames can be used to fit a greater number of patients. In such embodiments, because the anchors are configured to extend further from the frame, these prostheses are still able to securely grasp native tissue as the anchors can expand to different diameters depending on how they are constrained with a body cavity. In the context of a replacement heart valve, the frame (and the associated valve body) may have the same size across multiple patient sizes, and the anchors can either be configured to expand to different diameters, or different anchor arrangements may be used for different frames.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

Similarly, this method of disclosure, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:

1. A prosthesis configured to grasp intralumenal tissue when deployed within a body cavity, the prosthesis comprising:
   an expandable frame portion comprising a proximal end and a distal end and a longitudinal axis extending therethrough, the expandable frame portion comprising a plurality of foreshortening cells configured to collapse radially for delivery and to expand radially upon deployment, the expandable frame portion being configured to longitudinally foreshorten upon radial expansion;
   a plurality of proximal anchors extending from the expandable frame portion and expandable from a collapsed configuration to an expanded configuration, wherein in the expanded configuration, each proximal anchor extends proximally away from the proximal end of the expandable frame portion and then turns to extend radially outwardly from the expandable frame portion;
   a plurality of distal anchors extending from the expandable frame portion and expandable from a collapsed configuration to an expanded configuration, wherein in the expanded configuration, each distal anchor extends distally away from the distal end of the expandable frame portion and then turns to extend proximally, each distal anchor extending to an end positioned radially outward from the expandable frame portion; and
   a skirt comprising:
      a distal portion extending along an exterior of the expandable frame portion and the distal anchors; and
      a proximal portion sized to extend along at least a portion of the plurality of proximal anchors, wherein an end of the proximal portion is positioned further radially outward from the longitudinal axis than the ends of the distal anchors wherein the entirety of the proximal portion of the skirt is spaced distally from the proximal end of the expandable frame portion;
   wherein the proximal anchors and distal anchors are separated by the plurality of foreshortening cells such that the proximal anchors and distal anchors are configured to be drawn closer together along the longitudinal axis when the expandable frame portion foreshortens; and wherein each distal anchor extends distally from the expandable frame portion along a first segment, the first segment being substantially parallel with the longitudinal axis.

2. The prosthesis of claim 1, wherein at least some of the proximal anchors and/or distal anchors comprise looped ends.

3. The prosthesis of claim 1, wherein all of the plurality of proximal anchors and the plurality of distal anchors comprise looped ends.

4. The prosthesis of claim 2, wherein at least some of the anchors comprising looped ends are connected to the expandable frame portion at a first base and a second base spaced apart from each other.

5. The prosthesis of claim 2, wherein at least some of the anchors comprising looped ends are connected to the expandable frame portion by a single strut.

6. The prosthesis of claim 1, wherein the expandable frame portion, the plurality of proximal anchors and the plurality of distal anchors are formed from a single piece of material.

7. The prosthesis of claim 1, wherein the ends of at least some of the proximal anchors and/or distal anchors are substantially parallel with the longitudinal axis when the expandable frame portion is at least partially expanded and the proximal and distal anchors are in their expanded configurations.

8. The prosthesis of claim 1, wherein the ends of at least some of the proximal anchors are substantially perpendicular with the longitudinal axis when the expandable frame portion is at least partially expanded and the proximal anchors are in their expanded configurations.

9. A replacement mitral valve comprising the prosthesis of claim 1, wherein when the expandable frame portion is in an expanded configuration, the expandable frame portion is positionable within a native mitral valve annulus such that:
the distal anchors are positionable within the ventricle and have portions that extend generally proximally toward a ventricular side of the native mitral valve annulus.

10. The replacement mitral valve of claim 9, wherein the distal anchors are positionable within the ventricle and extend proximally to ends spaced distally from the native mitral valve annulus.

11. The replacement mitral valve of claim 9, wherein the distal anchors are positionable within the ventricle and extend proximally to ends that engage the native mitral valve annulus.

12. The replacement mitral valve of claim 9, wherein the proximal anchors atraumatically engage tissue on an atrial side of the native mitral valve annulus.

13. The prosthesis of claim 1, wherein each proximal anchor turns to extends distally after extending proximally from the proximal end of the expandable frame portion.

14. The prosthesis of claim 1, wherein each proximal anchor comprises a cell which extends proximally away from the proximal end of the expandable frame portion and then turns to extend radially outwardly from the expandable frame portion.

15. The prosthesis of claim 1, wherein in the expanded configuration, each of the plurality of distal anchors is bent to extend radially outwardly away from the first segment along a second segment and is then bent to extend proximally along a third segment.

16. The prosthesis of claim 1, wherein adjacent proximal anchors extend from a same corner of a foreshortening cell.

17. The prosthesis of claim 1, wherein the expandable frame portion comprises a first row of foreshortening cells and a second row of foreshortening cells, wherein the one or more foreshortening cells of the first row comprise a shape which is different from a shape of one or more of the foreshortening cells of the second row.

18. The prosthesis of claim 1, wherein the proximal anchors are each connected to the expandable frame portion at a first base and a second base spaced apart from each other and wherein a longitudinal strut extends between at least one of the proximal anchors.

19. The prosthesis of claim 1, wherein the plurality of distal anchors are approximately equally spaced around a periphery of the expandable frame portion.

20. A prosthesis configured to grasp intralumenal tissue when deployed within a native mitral valve, the prosthesis comprising:
an expandable frame portion comprising a proximal end and a distal end and a longitudinal axis extending therethrough, the expandable frame portion comprising a plurality of foreshortening cells configured to collapse radially for delivery and to expand radially upon deployment;
a proximal anchoring portion extending from the expandable frame portion and expandable from a collapsed configuration to an expanded configuration, wherein when the proximal anchoring portion is in an expanded configuration:
at least a portion of the proximal anchoring portion extends proximally; and
at least a portion of the proximal anchoring portion extends radially outwardly in a direction generally perpendicular to the longitudinal axis, the portion of the proximal anchoring portion that extends radially outwardly being sized and shaped to contact an atrial side of a native valve annulus;
a distal anchoring portion extending from the expandable frame portion and expandable from a collapsed configuration to an expanded configuration, the distal anchoring portion comprising a plurality of distal anchors which are each connected to the expandable frame portion at a first base and a second base spaced apart from each other, wherein when the distal anchoring portion is in an expanded configuration:
at least a portion of each distal anchor extends radially outward from the expandable frame portion; and
at least one distal anchor comprises at least one bend, the end of the at least one distal anchor extending toward the proximal end of the expandable frame portion; and
a skirt annularly positioned around an exterior of the expandable frame portion to create an axial barrier to fluid flow exterior to the expandable frame portion when deployed within the body cavity, the skirt comprising:
a first portion sized and shaped to extend along and follow the shape of the exterior of expandable frame portion when the expandable frame portion is in an expanded configuration, the first portion having a proximal end and a distal end,
a second portion configured to be positioned radially between the expandable frame portion and the distal anchoring portion when the expandable frame portion is in an expanded configuration, the second portion extending from the distal end of the first portion and extending at least along an inwardly facing surface of the distal anchoring portion; and a third portion extending radially outward from the expandable frame portion when the expandable frame portion is in an expanded configuration, the third portion extending radially outward from a location spaced from the proximal end of the expandable frame portion, the third portion extending from the proximal end of the first portion and extending along at least a portion of the plurality of proximal anchors, wherein an end of the third portion is positioned further radially outward from the longitudinal axis than the ends of the distal anchors; and a plurality of locking tabs extending proximally, wherein when the expandable frame portion is in an expanded configuration the plurality of locking tabs extend proximally of the expandable frame portion and the proximal anchoring portion.

21. The prosthesis of claim 20, wherein the expandable frame portion is configured to longitudinally foreshorten upon radial expansion and wherein the proximal anchoring portion and at least the plurality of anchors of the distal anchoring portion are separated by the plurality of foreshortening cells such that the proximal anchoring portion and at least the plurality of anchors of the distal anchoring portion are configured to be drawn closer together along the longitudinal axis when the expandable frame portion foreshortens.

22. The prosthesis of claim 20, wherein the third portion of the skirt extends in a direction generally perpendicular to the longitudinal axis.

23. The prosthesis of claim 20, wherein the third portion of the skirt forms an annular ring.

24. The prosthesis of claim 20, wherein the entirety of the third portion of the skirt is positioned distal of proximal ends of the foreshortening cells.

25. A prosthesis configured to grasp intralumenal tissue when deployed within a native mitral valve, the prosthesis comprising:

an expandable frame portion comprising a proximal end and a distal end and a longitudinal axis extending therethrough, the expandable frame portion comprising a proximal row of foreshortening cells and a distal row of foreshortening cells, the foreshortening cells configured to collapse radially for delivery and to expand radially upon deployment, the expandable frame portion being configured to longitudinally foreshorten upon radial expansion;

a plurality of proximal anchors extending from the expandable frame portion and expandable from a collapsed configuration to an expanded configuration, each of the proximal anchors extending from junctions between the proximal row of foreshortening cells, wherein in an expanded configuration, ends of the plurality of proximal anchors are positioned radially outwardly relative from the expandable frame portion and extend in a direction substantially perpendicular to the longitudinal axis, the ends being axially positioned distal of the proximal end of the expandable frame portion;

a plurality of distal anchors extending from the expandable frame portion and expandable from a collapsed configuration to an expanded configuration, each of the distal anchors connected to a base at a distal portion of the distal row of foreshortening cells, wherein in an expanded configuration, ends of the plurality of distal anchors are positioned radially outwardly relative from the expandable frame portion and the axial length between the base and the ends is less than a length of the cells of the distal row when in an expanded configuration; and a skirt annularly positioned around an exterior of the expandable frame portion to create an axial barrier to fluid flow exterior to the expandable frame portion when deployed within the body cavity, the skirt comprising:

a generally cylindrical portion having a proximal end and a distal end; and a ring-shaped portion extending radially outward from the frame at a location axially spaced from the proximal end to prevent axial flow of fluid around an exterior of the prosthesis, the ring-shaped portion comprising an inner edge extending from the proximal end of generally cylindrical portion of the skirt, the ring-shaped portion extending radially outwardly from the inner edge to an outer edge;

wherein the proximal anchors and distal anchors are configured to be drawn closer together along the longitudinal axis when the expandable frame portion foreshortens.

26. The prosthesis of claim 25, wherein the expandable frame portion comprises a plurality of longitudinally extending struts, wherein one or more of the longitudinally extending struts extends distally from an apex of a foreshortening cell and comprises at least one eyelet extending through the longitudinally extending strut for attaching a valve to the expandable frame.

* * * * *